United States Patent [19]

Asano et al.

[11] Patent Number: 4,849,345

[45] Date of Patent: Jul. 18, 1989

[54] L-PHENYLALANINE DEHYDROGENASE AND USE THEREOF

[75] Inventors: Yasuhisa Asano; Akiko Nakazawa, both of Sagamihara; Shiro Terashima, Tokyo; Kiyosi Kondo, Yamato; Kaori Endo, Fujisawa; Kenji Hirai; Naganori Numao, both of Sagamihara, all of Japan

[73] Assignee: Sagami Chemical Research Center, Tokyo, Japan

[21] Appl. No.: 851,207

[22] Filed: Apr. 14, 1986

[30] Foreign Application Priority Data

Apr. 17, 1985 [JP] Japan ................................ 60-80293
Jun. 13, 1985 [JP] Japan ................................ 60-127118
Dec. 5, 1985 [JP] Japan ................................ 60-272494

[51] Int. Cl.$^4$ ............................................. C12P 13/04
[52] U.S. Cl. .................................. 435/106; 435/108; 435/113; 435/189; 435/190; 435/252.5; 435/252.1; 435/832; 435/822
[58] Field of Search ............... 435/108, 189, 113, 190, 435/106, 252.1, 252.5, 822, 832

[56] References Cited

U.S. PATENT DOCUMENTS

| | | | |
|---|---|---|---|
| 3,036,958 | 5/1962 | Asai et al. | 135/108 |
| 3,133,868 | 5/1964 | Takesue et al. | 435/108 |
| 4,304,858 | 12/1981 | Wandrey et al. | 435/116 |
| 4,590,161 | 5/1986 | Kula et al. | 435/108 |

FOREIGN PATENT DOCUMENTS

| | | |
|---|---|---|
| 0023346 | 2/1981 | European Pat. Off. |
| 0120208 | 10/1984 | European Pat. Off. |
| 0151488 | 8/1985 | European Pat. Off. |
| 0188712 | 7/1986 | European Pat. Off. |
| 60-43391 | of 0000 | Japan |
| 59-198972 | 11/1984 | Japan |
| 60-160890 | 8/1985 | Japan |
| 60-164493 | 8/1985 | Japan |

OTHER PUBLICATIONS

Brock, T. D., *Biology of Microrganisus*. N. J. Prentice Hall, Inc., 1979, 3rd ed., pp. 101, 142–144.

American Type Culture Collection, Catalogue of Strains I, 15th ed., 1982, p. 194.

Agricultural and Biological Chemistry, vol. 49, No. 12, Dec. 1985.

*Primary Examiner*—Robert A. Wax
*Attorney, Agent, or Firm*—Wegner & Bretschneider

[57] ABSTRACT

New L-phenylalanine dehydrogenases produced by a microorganism belonging to the genus Sporosarcina or Bacillus, new microorganisms capable of l-phenylalanine dehydrogenase and belonging to the genus Sporosarcina or Bacillus, a process for production of L-phenylalanine dehydrogenase using the microorganisms, and processes for production of L-amino acids using the enzymes or the microorganisms.

19 Claims, 15 Drawing Sheets

ELECTRON MICROGRAPH OF CELLS OF
STRAIN SCRC-R04

ELECTRON MICROGRAPH OF CELL OF
STRAIN SCRC-R53b

ELECTRON MICROGRAPH OF CELL OF
STRAIN SCRC-R79a

ELECTRON MICROGRAPH OF CELLS OF
STRAIN SCRC-101A

ELECTRON MICROGRAPH OF CELL OF
STRAIN SCRC-114D

RELATIONSHIP BETWEEN ACTIVITY AND pH FOR ENZYME FROM STRAIN SCRC-RO4

A: OXIDATIVE DEAMINATION
B: REDUCTIVE AMINATION pH-STABILITY FOR ENZYME FROM STRAIN SCRC-R04

RELATIONSHIP BETWEEN ACTIVITY AND TEMPERATURE FOR ENZYME FROM STRAIN SCRC-R04

UV-SPECTRUM FOR ENZYME FROM SCRC-R04

A: POLYACRYLAMIDE GEL 7.5%, pH 8.4
B: SDS-POLYACRYLAMIDE GEL 10.0%, pH 7.2

ELECTROPHORESIS FOR ENZYME FROM STRAIN SCRC-R04

MICROGRAPH OF CRYSTALS OF ENZYME FROM STRAIN SCRC-R04 pH-STABILITY FOR ENZYME FROM STRAIN SCRC-R79a

RELATIONSHIP BETWEEN ACTIVITY AND TEMPERATURE FOR ENZYME FROM STRAIN SCRC-R79a

TEMPERATURE-STABILITY FOR ENZYME FROM STRAIN SCRC-R79a

UV-SPECTRUM FOR ENZYME FROM STRAIN SCRC-R79a

A: POLYACRYLAMIDE GEL 7.5%, pH 8.4
B: SDS-POLYACRYLAMIDE GEL 10.0%, pH 7.2

ELECTROPHORESIS FOR ENZYME FROM STRAIN SCRC-R79a

MICROGRAPH OF CRYSTALS OF ENZYME FROM STRAIN SCRC-R79a

L-PHENYLALANINE DEHYDROGENASE AND USE THEREOF

BACKGROUND OF THE INVENTION

1. Field of the Invention

The present invention is related to novel enzymes L-phenylalanine dehydrogenases, processes for the production thereof, microorganisms producing the new enzyme, and processes for the production of L-amino acids using the enzyme.

2. Description of the Related Art

Attempts have been made to produce L-amino acids using α-ketocarboxylic acid as a substrate. For example, a process for preparing L-glutamic acid by adding α-ketoglutarate and various kinds of amino acids to microbial cells (Katagiri et. al. *Amino Acid and Nucleic Acid*, 2, 18, 1960); a process for obtaining L-phenylalanine by adding L-glutamic acid or L-aspartic acid to a reaction mixture containing phenylpyruvic acid (Asai et. al., *Amino Acid and Nucleic Acid*, 2, 114 (1960); and a process for synthesizing L-tryptophan by adding L-glutamic acid or L-aspartic acid to a reaction mixture containing indolepyruvic acid (Aida et. al., *Journal of General and Applied Microbiology*, 4, 200, 1958, have been disclosed.

Japanese Unexamined Patent Publication No. 60-164493 describes a process for the production of L-phenylalanine by either culturing one of various kinds of microoorganisms with phenylpyruvic acid and an amino group donor, or incubating cells of that microorganism or a treated product of the cells with phenylpyruvic acid and an amino group donor. However, this specification does not disclose just what kind of enzymes participate in the reaction. Moreover, such processes employ amino acids, which are an expensive amino group donor.

All of the above-mentioned processes use, as an amino group donor of an aimed amino acid, another amino acid, and are fundamentally different from a process of the present invention which uses an ammonium ion as an amino group donor, which is not so expensive. Namely, the prior art processes are more expensive than the present process. Moreover, the enzymes involved in the prior art process are different from those of the present process.

Japanese Unexamined Patent Publication No. 60-43391 discloses a process for production of L-amino acid wherein a microorganism capable of converting an α-keto acid to a corresponding L-amino acid is cultured, and during the culturing, the α-keto acid is fed into the culturing medium to convert the α-keto acid to the L-amino acid. According to the reaction mechanism suggested in the specification, as an amino group donor for the formation of an aimed L-amino acid from a corresponding α-keto acid, L-glutamate is used, which means that the reaction is carried out by an amino transferase. Moreover, the application discloses only Brevibacterium, Corynebacterium, and *Escherichia coli* as microorganisms involved.

Japanese Unexamined Patent Publication No. 59-198972 describes L-phenylalanine dehydrogenase and a process for the production of L-α-amino carboxylic acid using that enzyme. However, the L-phenylalanine dehydrogenase described therein is derived from Brevibacterium, and the specification does not suggest that Sporosarcina and Bacillus produce a similar enzyme. Moreover, the disclosed L-phenylalanine dehydrogenase has a molecular weight of 130,000±10,000 and consists of subunits having a molecular weight of 66,000±5,000 and, therefore, is different from the present L-phenylalanine dehydrogenase.

Japanese Unexamined Patent Publication No. 60-160890 discloses a process for the production of L-phenylalanine by either culturing one of various kinds of microorganisms with phenylpyruvate in the presence of an energy source, an inorganic ammonium compound or urea, and oxygen, or by incubating a cultured product of the microorganism or treated product thereof with phenylpyruvate in the presence of an energy source, an inorganic ammonium compound or urea, and oxygen. However, the specification does not suggest the kind of enzymes involved in the process, and the process is supposed to be essentially a fermentation process, due to the necessity for the presence of oxygen. Moreover, the specification does not refer to Sporosarcina.

SUMMARY OF THE INVENTION

The present invention provides new enzymes, L-phenylalanine dehydrogenases, i.e., L-phenylalanine dehydrogenase characterized by, (1) catalyzing a reaction wherein L-phenylalanine, $NAD^+$, and $H_2O$ react to form phenylpyruvate, NADH and ammonium ion, and a reverse reaction thereof, (2) having a molecular weight of about 290,000 as determined by high performance liquid chromatography and a molecular weight of about 305,000 as determined by a sedimentation equilibrium method, and exhibiting a sub-unit with a molecular weight of about 38,000 to 39,000 as determined by SDS-polyacrylamide gel electrophoresis, and (3) acting strongly on L-phenylalanine, but act very weakly on L-tryptophan, L-tyrosine and L-methionine for oxidative deamination; L-phenylalanine dehydrogenase characterize by (1) catalyzing a reaction wherein L-phenylalanine, $NAD^+$ and $H_2O$ react to form phenylpyruvate, NADH and ammonium ion, and a reverse reaction thereof, and (2) being produced by a microorganism belonging to the genus Sporosarcina; L-phenylalanine dehydrogenase characterized by (1) catalyzing a reaction wherein L-phenylalaine, $NAD^+$ and $H_2O$ react to form phenylpyruvate, NADH and ammonium ion, and a reverse reaction thereof, (2) exhibiting a molecular weight of about 290,000 as determined by high performance liquid chromatography, a molecular weight of about 340,000 as determined by a sedimentation equilibrium method, and exhibiting a sub-unit with a molecular weight of about 38,000 to 39,000 as determined by SDS-polyacrylamide gel electrophoresis, and (3) acting strongly on L-phenylalanine and L-tyrosine, and acting very weakly on L-tryptophan and L-methionine for oxidative deamination; L-phenylalanine dehydrogenase characterized by (1) catalyzing a reaction wherein L-phenylalanine, $NAD^+$ and $H_2O$ react to form phenylpyruvate, NADH and ammonium ion, and (2) being produced by a microorganism belonging to the genus Bacillus.

The present invention also provides new microorganisms capable of producing the above-mentioned enzymes and belonging to the genus Sporosarcina or Bacillus.

The present invention also provides a process for the production of the above-mentioned enzymes, comprizing culturing the above-mentioned microorganism.

The present invention also provides new processes for the production of L-amino acids from corresponding α-ketocarboxylic acid, characterized by reacting α-ketocarboxylic acid or a salt thereof, ammonium ion and NADH in the presence of L-phenylalanine dehydrogenase derived from microorganism belonging to the genus Sporosarcina or Bacillus to form the L-amino acid, and recovering the L-amino acid; or reacting α-ketocarboxylic acid or a salt thereof, and an ammonium ion in the presence of a cultured broth, living cells or cells treated to an extent whereby enzyme systems necessary for the conversion of α-ketocarboxylic acid to a corresponding L-amino acid remin, derived from a microorganism belonging to the genus Sporosarcina and capable of producing L-phenylalanine dehydrogenase, and in the presence of an energy source to form the L-amino acid, and recovering the L-amino acid.

BRIEF DESCRIPTION OF THE DRAWINGS

FIG. 3 represents an electron micrograph of a cell of *Bacillus sp.* SCRC-R79a.

FIG. 14 is a graph showing pH-stability for L-phenylalanine dehydrogenase produced by *Bacillus sp.* SCRC-R79a.

FIG. 17 represents a UV spectrum for L-phenylalanine dehydrogenase produced by *Bacillus sp.* SCRC-R79a.

FIG. 19 represents a micrograph of crystals of L-phenylalanine dehydrogenase product by *Bacillus sp.* SCRC-R79a.

DESCRIPTION OF THE PREFERRED EMBODIMENT

1. Microorganism

Figure 1:
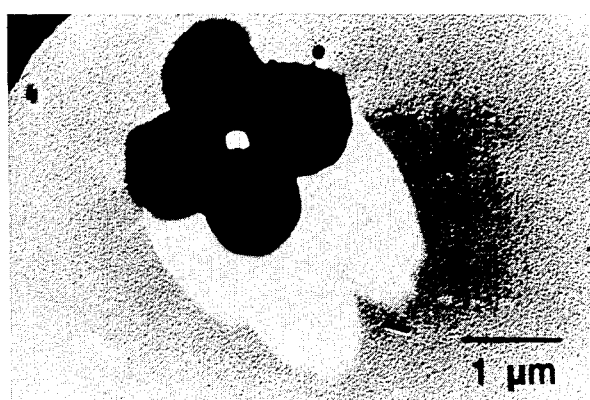
FIG. 1 represents an electron micrograph of cells of Sporosarcina ureae CSRC-R04.
Figure 2:
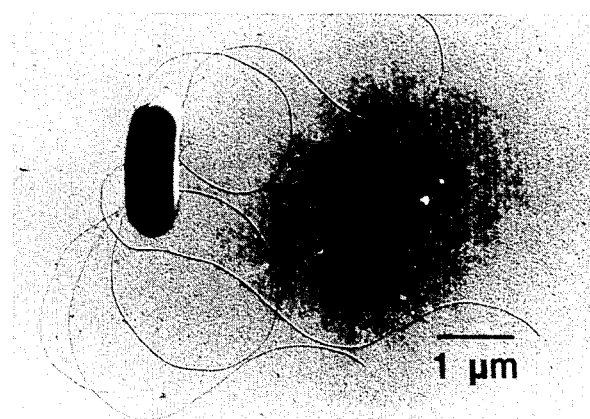
FIG. 2 represents an electron micrograph of a cell of *Bacillus sp.* SCRC-R53b.
Figure 3:
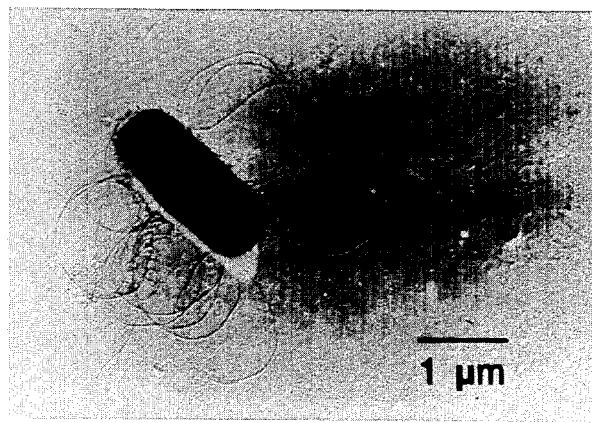
Figure 4:
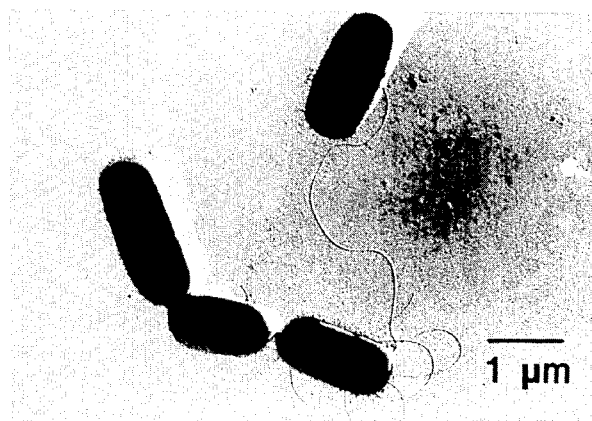
FIG. 4 represents an electron micrograph of cells of *Bacillus sp.* SCRC-101A.
Figure 5:
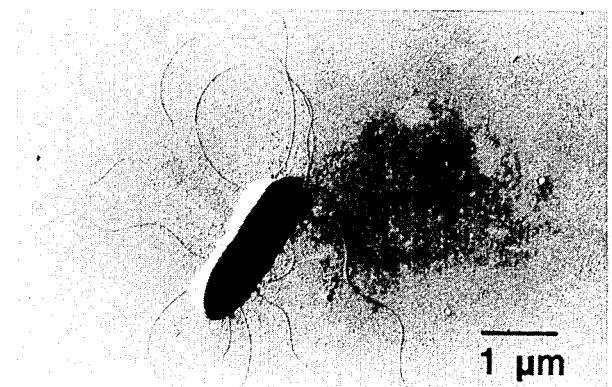
FIG. 5 represents an electron micrograph of a cell of *Bacillus sp.* SCRC-114D.

Microorganisms which can be used for the present invention are those belonging to the genus Sporosarcina or Bacillus and capable of producing L-phenylalanine dehydrogenase. Such microoorganisms may be selected from deposition libraries or may be isolated from natural sources.

The microorganisms belonging to genus Sporosarcina include *Sporosarcina ureae*. Such species include, for example, strains *Sporosarcina ureae* IFO 12698 and *Sporosarcina ureae* IFO 12699 (ATCC 6473) as species selected from deposition library, and *Sporosarcina ureae* SCRC-R04 first isolated by the present inventor. The former strains can be obtained from the Institute for Fermentation Osaka (IFO), 17-85 Juso-honmachi 2-chome, Yodogawa-ku, Osaka 532, Japan, or the American Type Culture Collection (ATCC), 12301, Parklawn Drive, Rockville, Md. 20852, U.S.A.; and the latter strain, *Sporosarcina ureae* SCRC-R04, was deposited with the Fermentation Research Institute Agency of Industrial Science and Technology, Minisry of International Trade and Industry (FRI), 1-1-3 Yatabe-cho Higashi, Tsukuba-gun, Ibaraki-ken, Japan, as FERM P-8178, on Apr. 16, 1985, and transferred to the international deposition under the Budapest Treaty on the International Recognition of the Deposit of Microorganisms for the Purpose of Patent Procedure ((Budapest Treaty) as FERM BP-1012 on Apr. 3, 1986.

The microorganisms which can be used in the present application belonging to genus Bacillus include, for example, *Bacillus alvei* IFO 3343; *Bacillus thiaminolyticus* IAM 1034 deposited with FRI as FERM P-8528 on Nov. 28, 1986; *Bacillus badius* IAM 11059, ATCC 14574, deposited with FRI as FERM P-8529 on Nov. 28, 1985; *Bacillus sphaericus* IFO 12622; *Bacillus sphaericus* IAM 1228, deposited with FRI as FERM P-8527 on Nov. 28, 1985. All of the above-mentioned strains are listed in catalogs published by the IFO, ATCC, or for IAM by the Japanese Federation of Culture Collections of Microorganisms (JFCC), Institute of Medical Science, University of Tokyo, Shiroganedai 4-6-1, Minato-ku, Tokyo 108, Japan, and are available to the public.

Moreover, the microorganism which can be used in the present invention includes new strains isolated by the present invention, such as *Bacillus sp.* SCRC-R53b; *Bacillus sp.* SCRC-R79a deposited with FRI as FERM P-8179 on Apr. 16, 1985, and transferred to the international deposition under the Budapest Treaty as FERM BP-1013 on Apr. 3, 1986; *Bacillus sp.* SCRC-101A; and *Bacillus sp.* SCRC 114D deposited with FRI as the international deposition FERM BP-1011 on Apr. 3, 1986.

The above-mentioned new strains belonging to Sporosarcina and Bacillus were isolated as follows: The culture medium with the following composition was prepared.

TABLE 1

| | |
|---|---|
| L—Phenylalanine | 1% |
| Peptone | 1% |
| Yeast extract | 0.5% |
| $K_2HPO_4$ | 0.2% |
| NaCl | 0.1% |
| $MgSO_4.7H_2O$ | 0.02% |
| City water | balance |
| | pH adjusted to 7.0 |

5 ml each of the medium was distributed into the test tubes ($\phi$18 mm), which were then sterilized at 120° C. for 15 minutes. To each of the test tubes, a small amount of soil sample was added, and the test tubes were incubated at 30° C. for three days, with shaking. A drop of the cultured broth was then inoculated to a new medium prepared as above, and culturing was carried out for three days at 30° C. with shaking. The second cultured broth was placed on agar plates, which are the above-mentioned medium supplemented with 2% agar, in streaks and the agar plates were incubated at 30° C. for several days until colonies of microorganisms developed. The colonies were then picked up and inoculated on slant agar media. As above-mentioned, many strains were isolated.

Next, 200 ml each of the medium with the composition set forth in Table 1 was incorporated to 500 ml-conical flasks, and sterilized as above. The strains obtained as above were cultured in the flasks for 24 hours at 30° C., with shaking, to obtain cultured cells. The cells were washed, and then disrupted by ultrasonic treatment. The treated products were centrifuged to obtain supernatants. The supernatants were dialyzed against an 0.01M phosphate buffer (pH 7.0) containing 0.1 mM EDTA and 5 mM 2-mercaptoethanol. The dialyzed supernatants were tested for L-phenylalanine dehydrogenase activity as described below.

As a result, five strains were obtained which remarkably produce L-phenylalanine dehydrogenase. These strains are listed in Table 2.

TABLE 2

| Strains | Origin of samples |
|---|---|
| SCRC-R04 | Sagamihara, Kanagawa, Japan |
| SCRC-R53b | Sagamihara, Kanagawa, Japan |
| SCRC-R79a | Sagamihara, Kanagawa, Japan |
| SCRC-101A | Matsudo, Chiba, Japan |
| SCRC-114D | Matsudo, Chiba, Japan |

The five above-listed strains have bacteriological characteristics as set forth in Table 3.

TABLE 3

| Observation | SCRC-RO4 | SCRC-R53b | SCRC-R79a | SCRC-101A | SCRC-114D |
|---|---|---|---|---|---|
| (a) Morphology | | | | | |
| 1 Shape of cell | 2 to 4 cocci | rod | rod | rod | rod |
| Size | 1.0~1.1 $\mu$m | 0.6 × 1.6 $\mu$m | 0.8 × 2.0 $\mu$m | 0.8 × 1.7 $\mu$m | 0.7 × 2.1 $\mu$m |
| 2 Polymorphism | none | none | none | none | none |
| 3 Motility | + | + | + | + | + |
| Flagella | polar | peritrichal | peritrichal | peritrichal | peritrichal |
| 4 Sporulation | + | + | + | + | + |
| Shape of sporangium | round | oval | oval | oval | oval |
| Location of sporangium | central | central or subterminal | central or subterminal | central or subterminal | central or subterminal |
| 5 Gram stain | + | + | + | + | + |
| 6 Acid resistance | − | − | − | − | − |
| (b) Growth characteristics | | | | | |
| 1 Bouillon agar plate (at 30° C., for 3 days) | | | | | |
| Size of colony | 4 mm | 6 mm | 1 cm | 1 cm | 4 mm |
| Shape of colony | round | round | round | round | round |
| | flat | convex | flat | flat | convex |
| Surface of colony | smooth | mucoid | rough | smooth | smooth |
| Edge of colony | entire | lobate | lobate | lobate | entire |
| Color of colony | brown or light yellow | white | white | white | yolk yellow |
| Transparency of colony | opaque | opaque | opaque | opaque | opaque |
| Gloss of colony | dull | dull | dull | dull | dull |
| Formation of soluble pigment | − | − | − | − | − |
| 2 Bouillon agar slant (at 30° C., for 3 days) | | | | | |
| Growth | abundant | abundant | abundant | moderate | moderate |
| Gloss of colony | dull | dull | dull | dull | dull |
| 3 Bouillion liquid (at 30° C., for 7 days) | | | | | |
| Growth at surface | none | present (islets) | present (islets) | none | none |
| Turbidity | slightly turbid | moderately turbid | moderately tyrbud | slightly turbid | slightly turbid |
| Precipitation | compact | flaky | flaky | compact | compact |
| Gas formation | none | none | none | none | none |
| 4 Bouillon gelatin (at 30° C., for 7 days) | | | | | |
| Gelatin liquefaction | none | liquefied | liquefied | liquefied | none |
| Litmus milk | no pH chang no liquefaction no coagulation | no pH chang no liquefaction no coagulation | no pH chang no liquefaction no coagulation | no pH chang no liquefaction no coagulation | no pH chang no liquefaction no coagulation |
| (c) Physiological properties | | | | | |
| 1 Nitrate reduction | + | − | − | − | − |
| 2 Denitrification | − | − | − | − | − |

TABLE 3-continued

| Observation | SCRC-RO4 | | SCRC-R53b | | SCRC-R79a | | SCRC-101A | | SCRC-114D | |
|---|---|---|---|---|---|---|---|---|---|---|
| 3 Methylred test | − | | − | | − | | − | | − | |
| 4 Voges-Proskauer test | − | | − | | − | | − | | − | |
| 5 Indole formation | − | | − | | − | | − | | − | |
| 6 Hydrogen sulfide formation | − | | − | | − | | − | | − | |
| 7 Amylolzability | − | | − | | − | | − | | − | |
| 8 Citric acid utilization | | | | | | | | | | |
| Koser | − | | − | | − | | − | | − | |
| Simmons | + | | − | | − | | − | | − | |
| Christensen | + | | − | | − | | − | | − | |
| 9 Nitrate utilization | − | | − | | − | | − | | − | |
| 10 Pigment formation | | | | | | | | | | |
| King A medium | − | | − | | − | | − | | − | |
| King B medium | − | | − | | − | | − | | − | |
| 11 Urease | + | | − | | − | | − | | − | |
| 12 Oxidase | − | | + | | + | | + | | + | |
| 13 Catalase | + | | + | | + | | + | | + | |
| 14 Growth range | | | | | | | | | | |
| pH | 6~10 | | 6~10 | | 6~10 | | 6~10 | | 7~11 | |
| Temperature | 5~32° C. | | 20~45° C. | | 20~45° C. | | 20~45° C. | | 10~37° C. | |
| 15 Oxygen requirement | aerobic | | aerobic | | aerobic | | aerobic | | aerobic | |
| 16 O-F test (glucose) | not acting on glucose | | alkaline | | alkaline | | alkaline | | not acting on glucose | |
| 17 Acid/gas formation from sugar | acid | gas | acid | gas | acid | gas | acid | gas | acid | gas |
| 1. L-Arabinose | − | − | − | − | − | − | − | − | − | − |
| 2. D-Xylose | − | − | − | − | − | − | − | − | − | − |
| 3. D-Glucose | − | − | − | − | − | − | − | − | − | − |
| 4. D-Mannose | − | − | − | − | − | − | − | − | − | − |
| 5. D-Fructose | − | − | − | − | − | − | − | − | − | − |
| 6. D-Galactose | − | − | − | − | − | − | − | − | − | − |
| 7. Maltose | − | − | − | − | − | − | − | − | − | − |
| 8. Sucrose | − | − | − | − | − | − | − | − | − | − |
| 9. Lactose | − | − | − | − | − | − | − | − | − | − |
| 10. Trehalose | − | − | − | − | − | − | − | − | − | − |
| 11. D-Sorbitol | − | − | − | − | − | − | − | − | − | − |
| 12. D-Mannitol | − | − | − | − | − | − | − | − | − | − |
| 13. Glycerin | − | − | − | − | − | − | − | − | − | − |
| 14. Starch | − | − | − | − | + | − | − | − | − | − |
| 15. Raffinose | − | − | − | − | − | − | − | − | − | − |
| 16. Inulin | − | − | − | − | − | − | − | − | − | − |
| 17. D-Ribose | − | − | − | − | − | − | − | − | − | − |
| 18. Sorbose | − | − | − | − | − | − | − | − | − | − |
| 19. Carboxymethylcellulose | − | − | − | − | − | − | − | − | − | − |
| 20. Glycogen | − | − | − | − | − | − | − | − | − | − |
| Other properties | | | | | | | | | | |
| Phosphatase | + | | | | | | | | + | |
| Tyrosinase | − | | + | | − | | − | | + | |
| DNase | − | | − | | − | | − | | + | |
| Decomposition of arginine | − | | − | | − | | | | − | |
| Gelatin liquefaction | − | | + | | + | | + | | − | |
| Vitamin requirement | biotin | | − | | − | | − | | thiamin | |
| Salt resistance | | | | | | | | | | |
| 5% | + | | + | | + | | + | | + | |
| 7% | + | | + | | + | | + | | + | |
| 10% | − | | − | | − | | − | | − | |
| Lipase | − | | | | | | | | | |
| Lectinase | | | | | | | | | | |
| Egg white coagulation | − | | | | | | − | | − | |
| Sensitivity to antibiotics | | | | | | | | | | |
| Penicillin G | + | | | | | | | | | |
| Streptomycin | + | | | | | | | | | |
| Chloramphenicol | + | | | | | | | | | |
| Tetracycline | + | | | | | | | | | |
| Novobiocin | − | | | | | | | | | |
| Polymyxin B | + | | | | | | | | | |
| Erythromycin | + | | | | | | | | | |

On the basis of the above-mentioned bacteriological properties, and according to the classification criteria described in Bergey's Manual of Determinative Bacteriology, the eighth edition, 1974, the above-listed strains were identified as follows:

(a) SCRC-R04 is aerobic, motile, capable of forming spores, Gram positive, and 2 to 4 cocci. Therefore the strain belongs to genus Sporosarcina. Since Sporosarcina includes *Sporosarcina ureae* as sole species, and the above-mentioned properties of SCRC-R04 are almost consistent with those described in the literature, the strain SCRC-R04 is identified to be *Sporosarcina ureae*.

(b) All SCRC-R53b, SCRC-R79a, SCRC-101A and SCRC-114D are Gram positive, rod, capable of forming endospores and forming catalase. Therefore, they belong to Bacillus.

Electron micrographs of cells of the strains SCRC-R04, SCRC-R53b, SCRC-R79a, SCRC-101A, and SCRC-114D are shown in FIGS. 1 to 5, respectively.

The above-mentioned strains for the present invention may be converted to strains having an enzyme productivity higher than the original strains, according to conventional mutation or selection. Moreover, a gene coding for L-phenylalanine dehydrogenase may be cut out and inserted into an appropriate vector such as a plasmid, which may be then used to transform a heterologous host such as *Escherichia coli,* or a homologous host such as Bacillus or Sporosarcina artificially to create strains exhibiting a higher productivity for L-phenylalanine dehydrogenase.

The microorganisms used in the present application can be preserved according to a conventional method, such as on an agar slant medium or by lyophilization. As an agar slant medium, a conventional medium for preservation of microorganism belonging to genus Bacillus or Sporosarcina, for example, the above-mentioned medium, may be used. Lyophilization also may be carried out according to a conventional method.

2. Enzyme L-Phenylalanine Dehydrogenase (1) Production of L-Phenylalanine Dehydrogenase For culturing the above-mentioned microorganisms to produce the L-phenylalanine dehydrogenase, any medium in which the present microorganisms grow may be used. The medium contains, as a nitrogen source, for example, yeast extract, peptone or meat extract, or a mixture thereof. Moreover, the medium may contain, as a carbon source, glucose, starch, or glycerin, etc. Preferably, the medium contains minerals, such as potassium phosphates, sodium chloride, and magnesium sulfate.

To stimulate the production of L-phenylalanine dehydrogenase, preferably a small amount of L-phenylalanine is added to a medium as an inducer. The amount of L-phenylalanine as the inducer varies, depending on the composition of the medium used, nature of the microorganism cultured, etc., and usually is 0.01 to 10% by weight, preferably 0.1 to 1% by weight, on the basis of the medium.

The medium may be a solid medium or a liquid medium, but for a large amount of production of the enzyme, the microorganism is cultured in a liquid medium in the aerobic condition achieved by shaking the medium, or agitation and aeration in the medium. The microorganism is cultured at any temperature at which the microorganism can grow and produce L-phenylalanine dehydrogenase. This temperature is preferably 25° C. to 45° C. The pH value of the medium is 6 to 9, preferably 7 to 10. Culturing usually is carried out for 6 to 48 hours.

L-phenylalanine is recovered and purified from the cultured broth according to a combination of conventional procedures used for the purification of an enzyme. For example, a cultured broth is centrifuged to collect bacterial cells. The cells are then disrupted by a conventional method such as ultrasonication or Dynomill treatment, and debris eliminated by a conventional method such as centrifugation or filtration to obtain a supernatant or filtrate containing the aimed enzyme. Further purification, for example, protamine sulfate treatment, streptomycin sulfate treatment, salting out, organic solvent precipitation, absorption chromatography, ion exchange chromatography, gel filtration chromatography, and crystallization using, for example, ammonium sulfate or polyethyleneglycol, may be used. Processes for the purification to crystallization of the present enzyme L-phenylalanine dehydrogenase are illustrated in Examples 1 to 3.

(2) Method of Determination of Activity of L-Phenylalanine Dehydrogenase

The activity of L-phenylalanine dehydrogenase is determined according to the following procedures.

Oxidative deamination

100 $\mu$ moles of glycine-KCl-KOH buffer (pH 10.5), 2.5 $\mu$ moles of $NAD^+$, 10 $\mu$ moles of L-phenylalanine, and an appropriate amount of sample are mixed to a total volume of 1 ml to react the components, and the increase of an amount of NADH is measured according to the increase of absorption at 340 nm. An amount of the enzyme which increases an amount of NADH by 1 $\mu$ mole per 1 minute is defined as 1 unit.

Reductive amination

100 $\mu$ moles of a buffer, 10 $\mu$ moles of sodium phenylpyruvate, and an appropriate amount of sample are mixed to a total volume of 1 ml to react the components, and the decrease of an amount of NADH is determined according to the decrease of absorption at 340 nm. An amount of the enzyme which decreases an amount of NADH by 1 $\mu$ mole per minute is defined as 1 unit.

The rate of reductive amination of the phenylpyruvate is, at an optimum pH, about 5.5 times higher than that of the oxidative deamination of L-phenylalanine. Therefore, for the same sample, the unit value determined by the reductive amination method is about 5.5 times higher than the unit value determined by the oxidative deamination method.

(3) Properties of L-Phenylalanine Dehydrogenase

L-phenylalanine dehydrogenase of the present invention have the following properties.

A. L-phenylalanine dehydrogenase produced by *Sporosarcina ureae* SCRC-R04

(1) Enzyme action

The enzyme catalyzes the following reaction:

(2) Specificity to substrates

When observing oxidative deamination, the enzyme does not act or acts only slightly on L-amino acids other than L-phenylalanine, as shown in Table 4.

TABLE 4

| Amino acid | Relative activity (%) |
|---|---|
| L—Phenylalanine | 100 |
| L—Tryptophan | 6.8 |
| L—Tyrosine (1.4 mM) | 5.4 |
| L—Methionine | 4.1 |
| L—Ethionine | 7.0 |
| L—Valine | 3.1 |
| L—Leucine | 2.3 |
| L—Isoleucine | 0.54 |
| L—β-Amino-n-butyric acid | 1.6 |
| L—Norvaline | 6.3 |
| L—Norleucine | 15 |

The substrate concentration is 10 mM, except for the L-tyrosine concentration which is 1.4 mM.

D-phenylalanine, L-alanine, L-histidine, L-arginine, L-lysine, L-ornithine, L-asparagine, L-aspartic acid, L-glutamine, L-glutamic acid, L-proline, L-serine, L- threonine, L-cysteine, and DL-phenylglycine cannot serve as a substrate.

$NAD^+$ is necessary as the coenzyme, and $NADP^+$ exhibits only about 3.9% activity relative to $NAD^+$.

(3) Optimum pH

Figure 6:
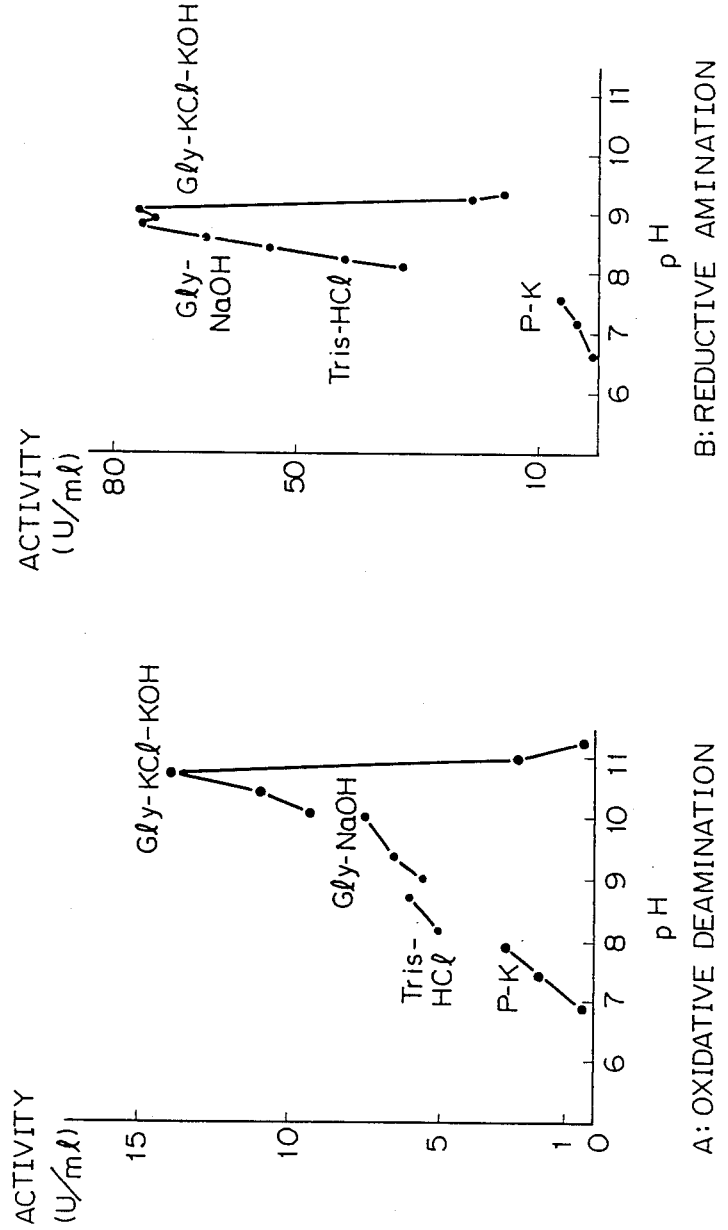
FIG. 6 contains graphs showing the relationship between pH and reaction rate for L-phenylalanine dehydrogenase produced by Sporosarcina ureae SCRC-R04, wherein A relates to oxidative deamination, and B relates to reductive amination.

For oxidative deamination, the optimum pH is about 10.5, and for reductive amination, the optimum pH is about 9.0, as shown in FIG. 6.

(4) pH-Stability

Figure 7:
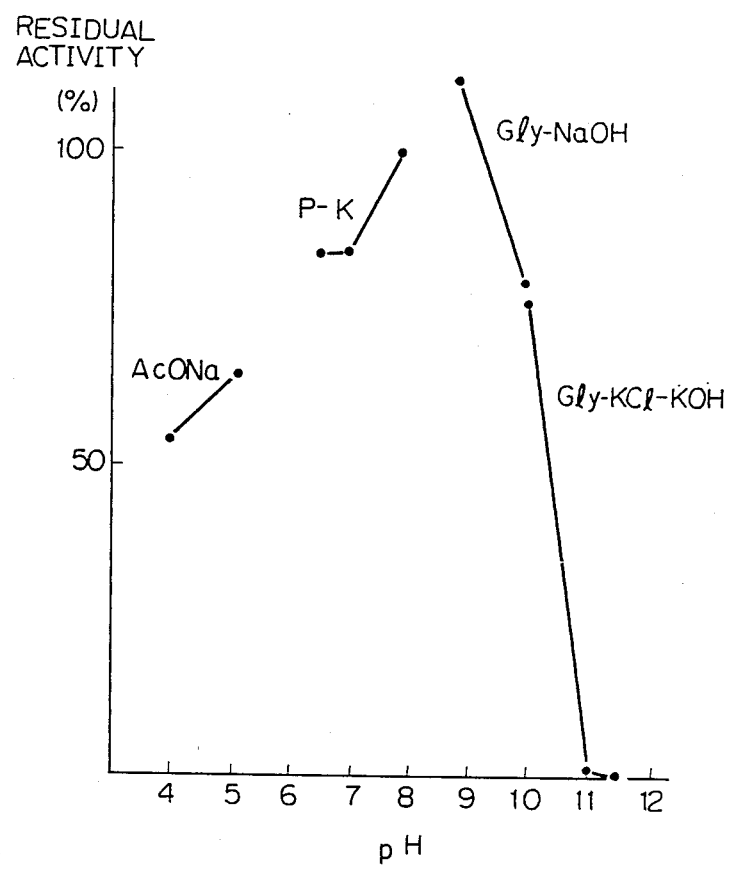
FIG. 7 is a graph showing pH-stability for L-phenylalanine dehydrogenase produced by Sporosarcina ureae SCRC-R04.

After incubation at 30° C. for 1 hour, the residual activity was determined for oxidative deamination. As shown in FIG. 7 (activity before treatment is 100%), the enzyme is the most stable at approximately pH 9.

(5) Optimum temperature

Figure 8:
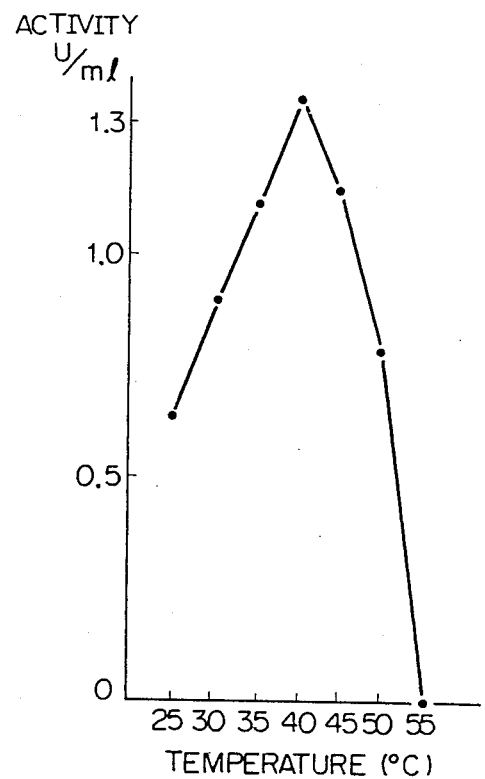
FIG. 8 is a graph showing the relationship between the temperature and reaction rate for L-phenylalanine dehydrogenase produced by *Sporosarcina ureae* SCRC-R04 for oxidation deamination.

The enzyme exhibits the highest activity at about 40° C., as shown in FIG. 8.

(6) Stability to temperature

Figure 9:
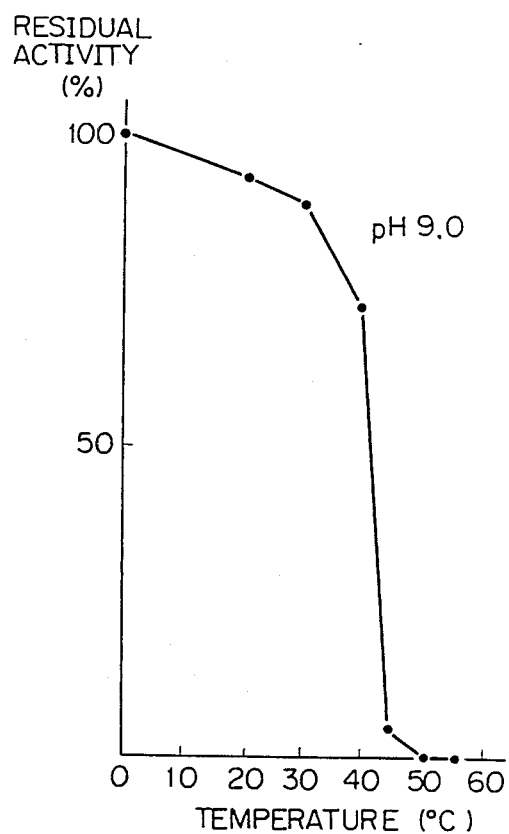
FIG. 9 is a graph showing temperature-stability for L-phenylalanine dehydrogenase produced by *Sporosarcina ureae* SCRC-R04.

After treating the enzyme at each temperature for 10 minutes in a 0.1M glycine-NaOH buffer (pH 9.0), the residual activity thereof is determined for oxidative deamination. A half of the initial activity is lost at 42° C., as shown in FIG. 9.

(7) Absorption spectrum

Figure 10:
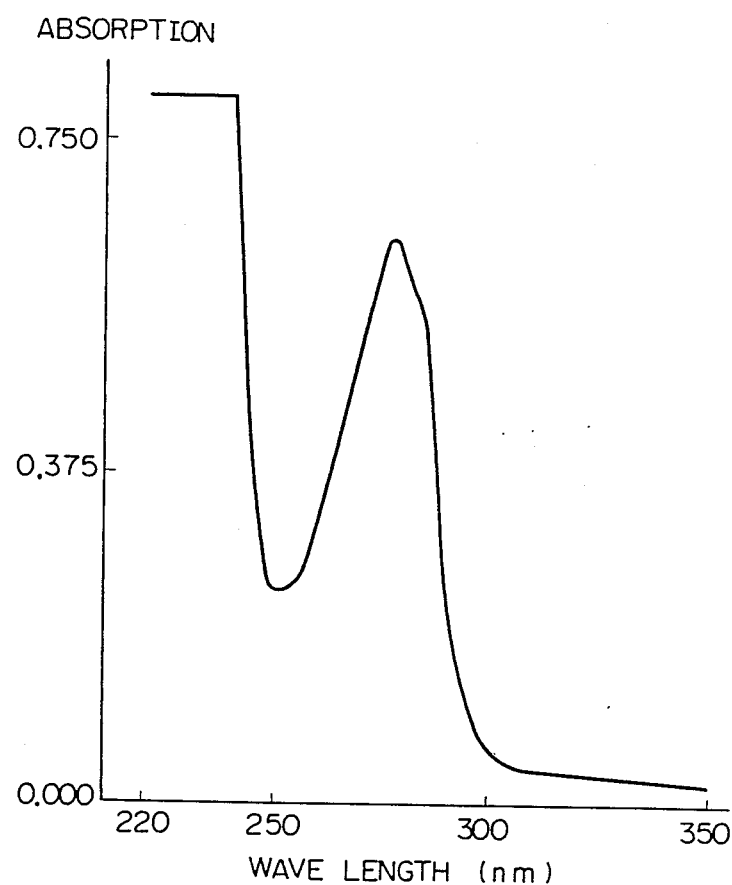
FIG. 10 represents a UV spectrum for L-phenylalanine dehydrogenase produced by *Sporosarcina ureae* SCRC-R04.

The maximum absorption is not 278 nm and a shoulder exits at 283 nm. Absorption at the visible light range is not observed. The absorption profile is shown in FIG. 10.

(8) Effect of metal ions and inhibitors

Enzyme activity is inhibited by metal cations such as silver cation, mercury cation, etc., and SH-inhibitors such as PCMB, N-ethylmaleimide, 5,5'-dithio-bis(2-nitrobenzoic acid) act as shown in Table 5.

TABLE 5

| Metal cation | Relative activity |
|---|---|
| $Li^+$ | 96% |
| $Na^+$ | 92 |
| $Ag^+$ | 0 |
| $Mg^{2+}$ | 90 |
| $Ca^{2+}$ | 100 |
| $Cu^{2+}$ | 91 |
| $Mn^{2+}$ | 129 |
| $Zn^{2+}$ | 99 |
| $Ni^{2+}$ | 100 |
| $Fe^{2+}$ | 127 |
| $Ba^{2+}$ | 106 |
| $Cd^{2+}$ | 70 |
| $Pb^{2+}$ | 81 |
| $Sn^{2+}$ (0.5 mM) | 123 |
| $Hg^{2+}$ (0.01 mM) | 0 |
| $Al^{3+}$ | 153 |
| $Fe^{3+}$ | 161 |
| Not added | 100 |
| $NaN_3$ | 100% |
| Hydroxylamine (10 mM) | 173 |
| KCN (0.5 mM) | 102 |
| o-Phenanthroline | 103 |
| α,α'-Dipyridyl | 124 |
| 8-Oxyquinoline | 101 |
| EDTA | 119 |
| PCMB (0.2 mM) | 0 |
| 5,5'-Dithio-bis(2-nitrobenzoic acid) | 0 |
| N—Ethylmaleimide | 21 |
| Iodoacetic acid | 91 |
| Not added | 100 |

Unless otherwise described, the concentration of metal cations and inhibitors is 1 mM.

(9) Isoelectric point

The isoelectric point is 5.3 to 5.4 as measured by isoelectric focusing using Ampholine.

(10) Molecular weight

This is determined to be about 290,000 as measured by high performance liquid chromatography (TSK 3000 SW), and about 305,000 as measured by the sedimentation equilibrium method.

(11) Molecular weight of sub-unit

This is determined to be about 38,000 to 39,000 as measured by SDS-polyacrylamid disc gel electrophoresis.

(12) Homogeneity

Figure 11:
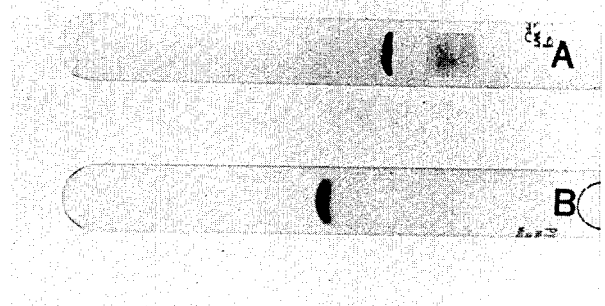
FIG. 11 is a photograph demonstrating the homogeneity of L-phenylalanine dehydrogenase produced by *Sporosarcina urea* SCRC-R04, wherein A represents a result of polyacrylamide gel electrophoresis (7.5% gel, pH 8.4), and B represents a result of SDS-polyacrylamide gel electrophoresis (10.0% gel, pH 7.2).

Polyacrylamide gel electrophoresis (7.5% gel, pH 8.4) provides a single band, as shown in FIG. 11A, and SDS-polyacrylamide gel electrophoresis (10.0% gel, pH 7.2) also provides a single band, as shown in FIG. 11B.

(13) Crystal form

Figure 12:
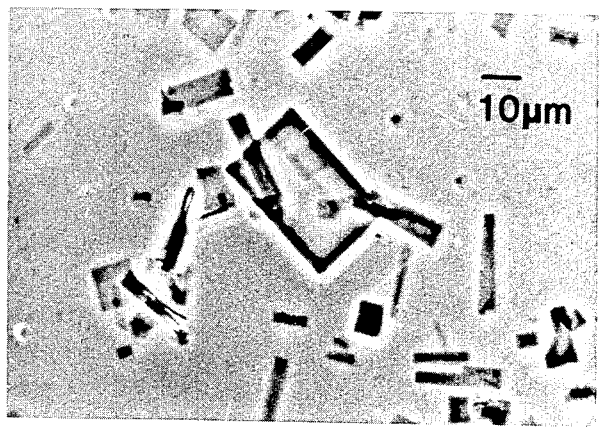
FIG. 12 represents a micrograph of crystals of L-phenylalanine dehydrogenase produced by *Sporosarcina ureae* SCRC-R04.

Plate as shown in FIG. 12.

B. L-phenylalanine dehydrogenase produced by *Bacillus sp.* SCRC-R79a (1) Enzyme action The enzyme catalyzes the following reaction:

L-phenylalanine + $NAD^+$ + $H_2O$ ⇌ phenylpyruvate + NADH + $NH_3$ + $H^+$ (2) Specificity to substrates When observing oxidative deamination, the enzyme does not act or acts only slightly on L-amino acids other than L-phenylalanine and L-tyrosine, as shown in Table 6.

TABLE 6

| Amino acid | Relative activity (%) |
|---|---|
| L—Phenylalanine | 100 |
| L—Trosine (1.4 mM) | 72 |
| L—Tryptaphan | 1.6 |
| L—Methionine | 3.0 |
| L—Ethionine | 3.1 |
| L—Norvaline | 1.3 |
| L—Norleucine | 3.9 |

The substrate concentration is 10 mM except for the L-tyrosine concentration which is 1.4 mM.

D-phenylalanine, L-alanine, L-histidine, L-arginine, L-lysine, L-ornithine, L-asparagine, L-aspartic acid, L-glutamine, L-glutamic acid, L-proline, L-serine, L-threonine, L-cysteine, L-valine, L-leucine, L-isoleucine, and L-α-amino-n-butyric acid cannot serve as a substrate.

The relative rate of converting 4-hydroxyphenypylruvate to L-tyrosine is 176% at pH 9.0 relative to the rate of converting phenylpyruvate to L-phenylalanine as 100%.

$NAD^+$ is necessary as a coenzyme, and $NADP^+$ exhibits only about a 2.9% activity relative to $NAD^+$.

(3) Optimum pH

Figure 13:
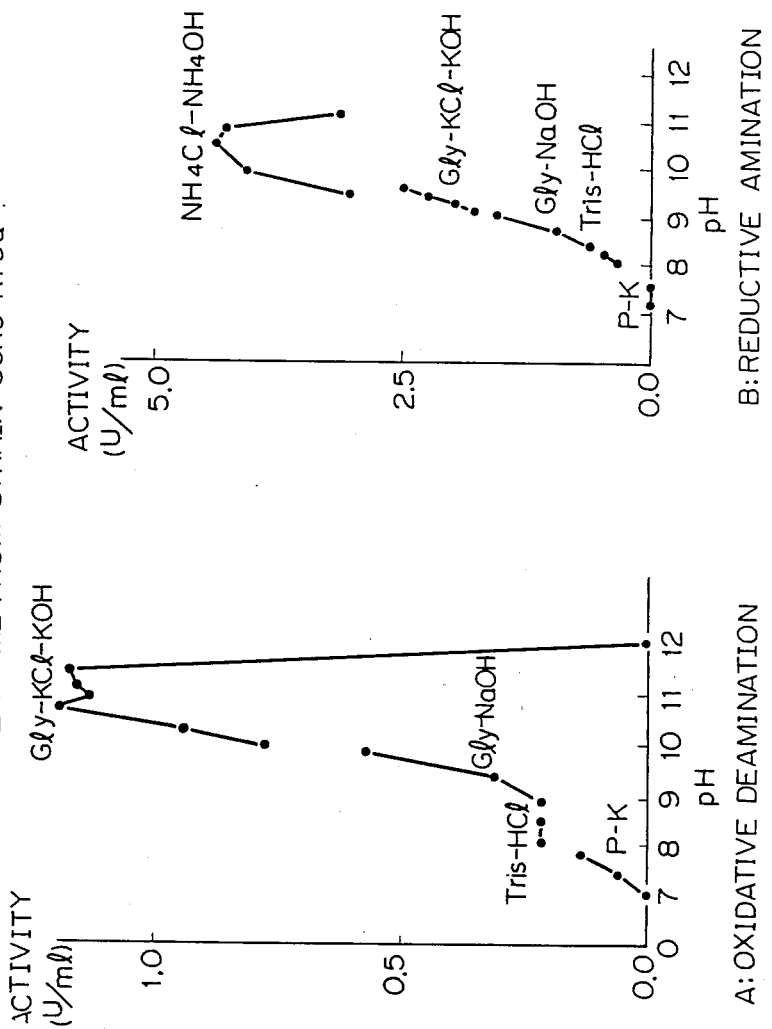
FIG. 13 contains graphs showing the relationship between pH and reaction rate for L-phenylalanine dehydrogenase produced by *Bacillus sp.* SCRC-R79a, wherein A relates to oxidative deamination, and B relates to reductive amination.

For oxidation deamination, the optimum pH is about 10.6 to 11.3, while for reductive amination, optimum pH is about 9.8 to 10.8, as shown in FIG. 13.

(4) pH-Stability

Figure 14:
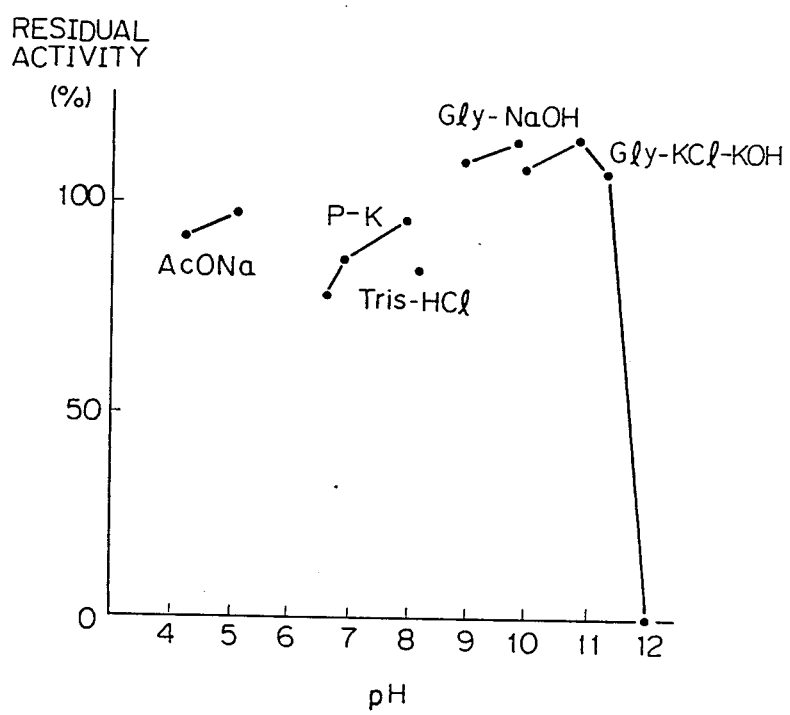

After incubation at 30° C. for 1 hour, the residual activity is determined for oxidative deamination. As shown in FIG. 14 (activity before treatment is 100%), the enzyme is stable at approximately pH 4.0 to 11.3, and especially pH 9 to 11.

(5) Optimum temperature

Figure 15:
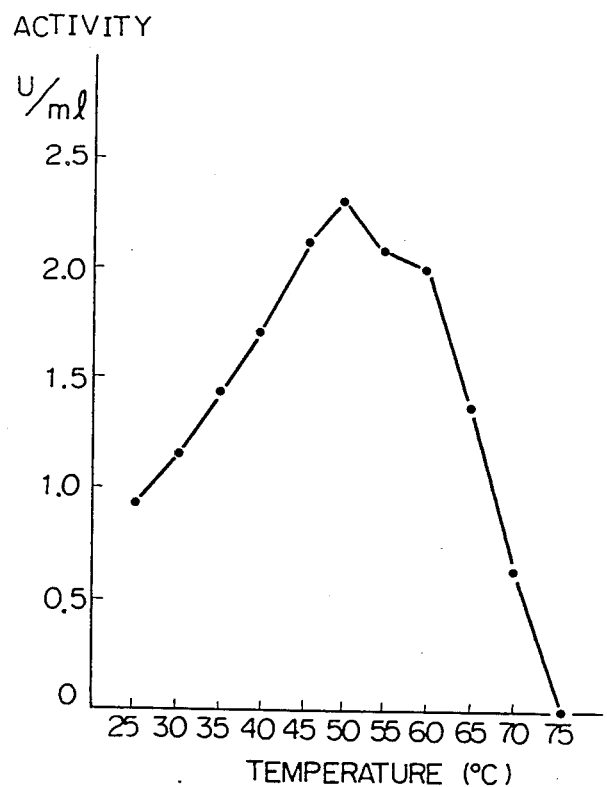
FIG. 15 is a graph showing the relationship between temperature and reaction rate for L-phenylalanine dehydrogenase produced by *Bacillus sp.* SCRC-R79a for oxidative deamination.

The enzyme exhibits the highest activity at about 50° C., as shown in FIG. 15.

(6) Stability to temperature

Figure 16:
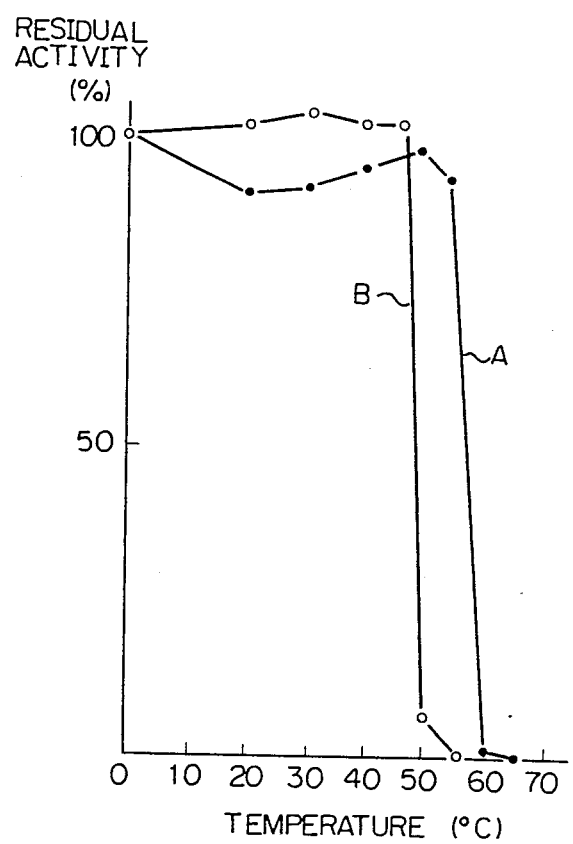
FIG. 16 is a graph showing temperature-stability for L-phenylalanine dehydrogenase produced by Bacillus sp. SCRC-R79a, wherein A represents a result obtained using 0.1M glycine-NaOH buffer (pH 9.0), and B represents a result obtained using 0.1M glycine-KCL-KOH buffer (pH 11.0).

After treating the enzyme at each treatment for 10 minutes, in a 0.1M glycine-NaOH buffer (pH 9.0, FIG. 16A), or in 0.1M glycine-KCl-KOH buffer (pH 11.0, FIG. 16B), the residual activity thereof is determined for oxidative deamination. At pH 9.0 and 57° C., or at pH 11.0 and 48° C., a half of the initial activity is lost.

(7) Absorption spectrum

Figure 17:
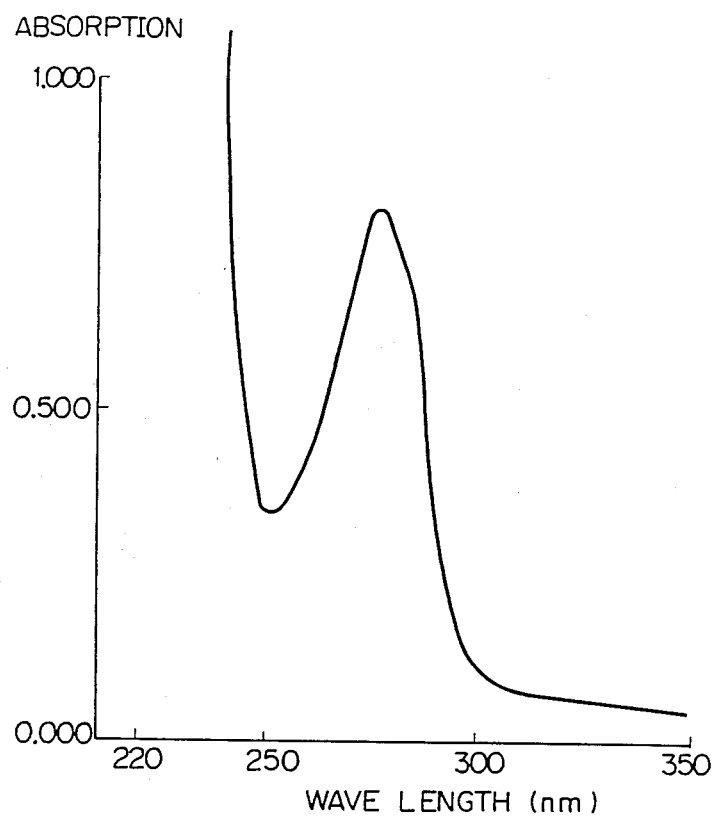

The maximum absorption is at 278 nm and a shoulder exists at 283 nm. Absorption at a visible light range is not observed. The absorption profile is shown in FIG. 17.

(8) Effect of metal ions and inhibitors

Enzyme activity is inhibited by metal cations such as silver cation, mercury cation, etc., and PCMB, as shown in Table 7.

TABLE 7

| Metal cation | Relative activity |
|---|---|
| $Li^+$ | 95% |
| $Na^+$ | 93 |
| $Ag^+$ | 0 |
| $Mg^{2+}$ | 99 |
| $Ca^{2+}$ | 92 |
| $Cu^{2+}$ | 85 |
| $Mn^{2+}$ | 95 |
| $Zn^{2+}$ | 96 |
| $Ni^{2+}$ | 100 |
| $Fe^{2+}$ | 116 |
| $Ba^{2+}$ | 93 |
| $Cd^{2+}$ | 102 |
| $Pb^{2+}$ | 53 |
| $Sn^{2+}$ (0.5 mM) | 110 |
| $Hg^{2+}$ (0.01 mM) | 38 |
| $Al^{3+}$ | 99 |
| $Fe^{3+}$ | 117 |
| Not added | 100 |
| $NaN_3$ | 102% |
| Hydroxylamine (10 mM) | 90 |
| KCN (0.5 mM) | 113 |
| o-Phenanthroline | 99 |
| α,α'-Dipyridyl | 104 |
| 8-Oxyquinoline | 96 |
| EDTA | 120 |
| PCMB (0.2 mM) | 0 |
| 5,5'-Dithio-bis(2-nitrobenzoic acid) | 74 |
| N—Ethylmaleimide | 162 |
| Iodoacetic acid | 127 |
| Not added | 100 |

Unless otherwise described, the concentration of metal cations and inhibitors is 1 mM.

(9) Isoelectric point

The isoelectric point is 4.3 to 4.4 as measured by isoelectric focusing using Ampholine.

(10) Molecular weight

This is determined to be about 290,000 as measured by high performance liquid chromatography (TSK 3000 SW), and about 340,000 as measured by sedimentation equilibrium method.

(11) Molecular weight of sub-unit

This is determined to be about 38,000 to 39,000 as measured by SDS-polyacrylamide disc gel electrophoresis.

(12) Homogeneity

Figure 18:
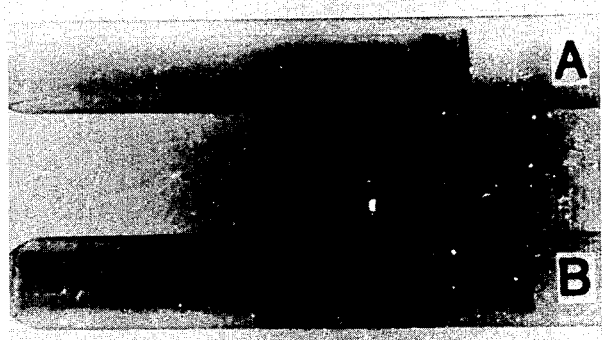
FIG. 18 is a photograph demonstrating the homogeneity of L-phenylalanine dehydrogenase produced by *Bacillus sp.* SCRC-R79a, wherein A represents a result of polyacrylamide gel electrophoresis (7.5% gel, pH 8.4), and B represents a result of SDS-polyacrylamide gel electrophoresis (10.0% gel, pH 7.2).

Polyacrylamide gel electrophoresis (7.5% gel, pH 8.4) provides a single band, as shown in FIG. 18A, and SDS-polyacrylamide gel electrophoresis (10.0% gel, pH 7.2) also provides a single band as shown in FIG. 18B.

Figure 19:
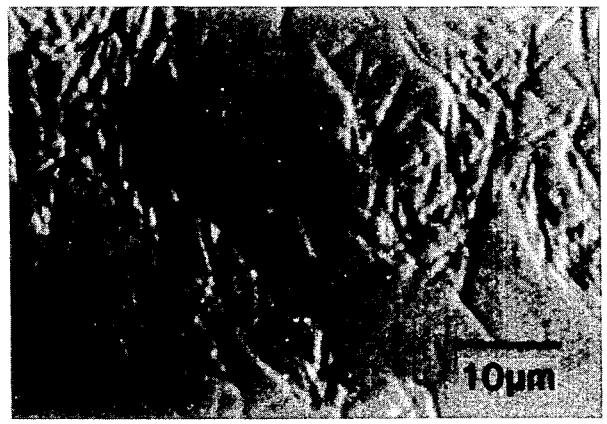

(13) Crystal form Needle as shown in FIG. 19.

On the basis of the above-mentioned enzymological properties, the L-phenylalanine dehydrogenases are deemed to be novel.

3. Process for Production of L-Amino Acids

The present invention also provides a process for the production of L-amino acid from α-ketocarboxylic acid involving the L-phenylalanine dehydrogenase.

The starting α-ketocarboxylic acids are represented by the following general formula (II):

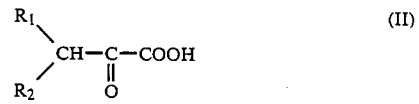

wherein $R_1$ represents hydrogen, or a lower alkyl group such as methyl; and $R_2$ repersents a linear or branched optionally substituted alkyl having 1 to 4 carbon atoms, or an optionally substituted aromatic group.

Substitutents for the alkyl group included, for example, hydroxyl, methylthio, methyl, and mercapto. The aromatic groups are, in particular, the phenyl and naphthyl groups. Substituents for the aromatic group include, for example, hydroxyl, halogen such as fluoro, chloro, bromo or iodo, vinyl, methoxy, nitro, a lower alkylthio, and a lower alkyl group. These substituents optionally again substituted.

From the above-mentioned α-ketocarboxylic acid, corresponding L-amino acids represented by the following general formula (I):

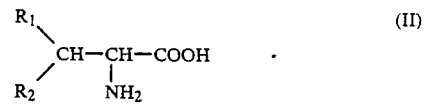

wherein $R_1$ and $R_2$ are the same as defined above, are formed.

As examples of starting α-ketocarboxylic acids, the following compounds are mentioned: phenylpyruvic acid, 4-hydroxyphenylpyruvic acid, 2-fluorophenylpyruvic acid, 3-fluorophenylpyrovic acid, 4-fluorophenylpyruvic acid, 3,4-difluorophenylpyruvic acid, 2-chlorophenylpyruvic acid, 3-chlorophenylpyruvic acid, 4-chlorophenylpyruvic acid, 3,4-dichlorophenylpyruvic acid, 4-methylphenylpyruvic acid, 4-vinylphenylpyruvic acid, 4-methoxyphenylpyruvic acid, 3,4-dimethoxyphenylpyruvic acid, 2,3,4-trimethoxyphenylpyruvic acid, 4-nitrophenylpyruvic acid, 4-di-(2-chloroethyl)amino-phenylpyruvic acid, indolepyruvic acid, α-keto-γ-methylthiobutyric acid, α-keto-γ-ethylthiobutyric acid, α-ketocaproic acid, α-ketoisocaproic acid, DL-αketo-β-methylvaleric acid, α-ketovaleric acid, α-ketoisovaleric acid, α-ketobutyric acid, 3-(β-naphthyl)pyruvic acid, 3,4-dimethylphenylpyruvic acid, 3-methoxyphenylpyruvic acid, and α-keto-γ-trifluoromethylbutyric acid.

From the above-mentioned starting α-ketocarboxylic acids, the following L-amimo acids are produced, respectively: L-phenylalanine, L-tyrosine, 2-fluoro-L-phenylalanine, 3-fluoro-L-phenylalanine, 4-fluoro-L-phenylalanine, 3,4-difluoro-L-phenylalanine, 2-chloro-L-phenylalanine, 3-chloro-L-phenylalanine, 4-chloro-L-phenylalanine, 3,4-dichloro-L-phenylalanine, 4-methyl-L-phenylalanine, 4-vinyl-L-phenylalanine, 4-methoxy-L-phenylalanine, 3,4-dimethoxy-L-phenylalanine, 2,3,4-trimethoxy-L-phenylalanine, 4-nitro-L-phenylalanine, 4-di-(2-chloroethyl)amino-L-phenylalanine, L-tryptophan, L-methionine, L-ethionine, L-norleucine, L-leucin, L-isoleucine, L-norvaline, L-valine, α-amino-L-butyric acid, 3-(β-naphthyl)-L-alanine, 3,4-dimethyl-L-phenylalanine, 3-methoxy-L-phenylalanine, and α-amino-γ-trifluoromethylbutyric acid.

According to one embodiment of the present process, an α-ketocarboxylic acid, NADH and ammonium ion are reacted under the pressure of L-phenylalanine dehydrogenase to form a corresponding L-amino acid, and the L-amino acid is recovered.

The forms of the enzyme preparations of L-phenylalanine dehydrogenase are not limited. The preparations include, for example, a completely purified enzyme; cultured broth containing cells; living cells; dried cell powders prepared by treating cells with, for example; acetone or ethanol; disrupted cells; partially purified enzyme preparations purified to various purification stages. Moreover, immobilized enzyme preparations, such as immobilized enzyme and immobilized enzyme-containing products prepared according to conventional procedures may be used.

An amount in a reaction medium of L-phenylalanine dehydrogenase derived from the above-mentioned enzyme preparation is not critical, but conveniently is within about 10 to 10,000 units per 1 litter, depending on the nature and amount of substrate α-ketocarboxylic acid and other conditions.

As a substrate, both α-ketocarboxylic acid and its salt may be used. The salts include, for example, sodium salt, potassium salt, lithium salt, and calcium salt, etc. An amount of α-ketocarboxylic acid or salt thereof in the reaction medium is not critical, but is conveniently about 1 to 500 g/l depending on the concentration of the enzyme. When the substrate is used in a lower concentration, it can be used as free acid, and when it is used in a relatively high concentration, it may be preferably used as a salt to simplify adjustment of pH of reaction medium. Sodium salt of various α-ketocarboxylic acids in a high concentration are not dissolved. However, the presence of solid salt in the reaction medium is not disadvantageous. When an ammonium salt of α-ketocarboxylic acid is used, the ammonium salt may act as a source of ammonium ion as well as a source of α-ketocarboxylic acid. In the batch-wise reaction, α-ketocarboxylic acid or salt thereof may be added to the reaction medium at one time at the start of the reaction, or added in portions or continuously during the reaction. Salts of α-ketocarboxylic acid may be those commercially available or those prepared by neutralization of a corresponding α-ketocarboxylic acid with a corresponding base, such as sodium hydroxide or ammonia.

As a source of ammonium ion, an ammonium salt, such as ammonium chloride or ammonium sulfate may be used. Moreover, ammonia gas or a aqueous ammonium hydroxide may be introduced in the reaction medium to maintain the pH value within a predetermined range. As described above, when an ammonium salt of α-keto-carboxylic acid is used as a substrate, the salt also serves as a source of ammonium ion. An amount of ammonium ion used is stoichiometric or more, in relation to the mol amount of α-ketocarboxylic acid used, and more specifically, about 1 to 100 mol amount in relation to the mol amount of α-ketocarboxylic acid used. By increasing an amount of ammonium salt used, the equilibrium of the enzyme reaction involved is forced to the side of L-amino acid formation, resulting in an increase in the yield of L-amino acid in relation to α-ketocarboxylic acid.

NADH may be used in an equivalent amount with α-ketocarboxylic acid. Since NADH is very expensive, however, from the industrial point of view, in addition to the reaction system wherein α-ketocarboxylic acid is reductively aminated with $NH_4^+$ and NADH to form L-amino acid and $NAD^+$, an NADH regenerating system wherein the $NAD^+$ formed is re-reduced to NADH is preferably used. As such an NADH regenerating system, a combination of an enzyme which converts $NAD^+$ to NADH and a substrate for the reaction, for example, a combination of formate dehydrogenase (EC 1.2.1.2) and formate, L-glutamate dehydrogenase (EC 1.4.1.2) and L-glutamate, alcohol dehydrogenase (EC 1.1.1.1) and ethanol, aldehyde dehydrogenase (EC 1.2.1.3) and acetaldehyde, or a combination of glucose-6-phosphate dehydrogenase (EC 1.1.1.49) and glucose-6-phosphate may be used. Moreover, the reduction of $NAD^+$ to NADH with hydrogenase (EC 1.18.3.1) using molecular hydrogen as an electron donor or the reduction of $NAD^+$ to NADH accompanied by the oxidation of methylbiologen or dihydrolipoamide with diaphorase (EC 1.6.4.3) may be used. Where formate dehydrogenase and formate are used, simultaneously with the reduction of $NAD^+$ to NADH, formic acid is oxidized to cardon dioxide gas, which is easily eliminated from the reaction system, resulting in the equilibrium of the reaction being forced in the desired direction. Therefore, as the NADH regenerating system, the combination of formate dehydrogenase and formate is especially preferable.

Formate dehydrogenase is commercially available, or prepared from *Candida boidinii* No. 2201 (AKU 4705) or *Hansenula polymorpha* ATCC 26012 according to a known procedure described by Kato et al., *Agricultural and Biological Chemistry*, 38, 111–116 (1974). Where formate dehydrogenase is used in the form cells containing the same, the treatment of the cells can be carried out according to a known procedure described by Izumi et al. in *Journal of Fermentation Technology*, 61, 135–142 (1983).

A concentration of enzyme for the NADH regenerating system varies, depending on a concentration of L-phenylalanine dehydrogenase, etc., and is generally a concentration at which $NAD^+$ is reduced to NADH at a rate corresponding to a rate at which an α-ketocarboxylic acid is reductively aminated, i.e., $NAD^+$ is formed. For example, where formate dehydrogenase is used as an enzyme for the NADH regenerating system in combination with 10 to 10,000 units/*l* of L-phenylalanine dehydrogenase, the concentration of the formate dehydrogenase is preferably about 10 to 10,000 units/*l*. As a substrate for formate dehydrogenase, a salt of formic acid, such as sodium formate, potassium formate or ammonium formate is conveniently used. An amount of formate is preferably a one to two equivalent amount of the α-ketocarboxylate used. Where the NADH regenerating system is used, $NAD^+$ or NADH may be added to 0.1 to 10 mM, which is a usual physiological concentration.

As a reaction medium, water or various kinds of an aqueous solution, for example, an aqueous buffer solution, or an aqueous solution containing an organic solvent such as acetone, acetonitrile, dimethylsulfoxide or dimethylformamide may be used. The buffer solutions include Tris-HCl buffer, glycine-NaOH buffer, etc.

Where the NADH regenerating system is not used, reaction is carried out at a pH suitable for the reductive amination of α-ketocarboxylic acid by the L-phenylalanine dehydrogenase used. L-phenylalanine dehydrogenase derived from Sporosarcina is used at pH 8 to 10, preferably approximately at pH 9, while L-phenylalanine dehydrogenase derived from Bacillus is used at pH 9 to 11, preferably approximately at pH 10. Where the NADH regenerating system is used in combination with the reductive amination of α-ketocarboxylic acid, the pH value of the reaction medium is selected within the range wherein both the reductive amination of α-ketocarboxylic acid and the reduction of NAD+ to NADH proceed satisfactorily. Such a pH range is that where a combination of L-phenylalanine dehydrogenase from Sporosarcina and formate dephydrogenase from *Candida boidinii* is used, usually pH 7.5 to 9.5, preferably pH 8.0 to 9.0; while where a combination of L-phenylalanine dehydrogenase from Bacillus and formate dehydrogenase from *Candida boidinni* is used, the pH range is usually 8 to 10, preferably 8.5 to 9.5.

Reaction temperature is selected under the same consideration as for the selection of the pH range. The reaction temperature is usually 20° C. to 50° C., preferably 25° C. to 40° C.

The reaction term is not critical, and is selected so that a substrate α-ketocarboxylic acid is converted to a product L-amino acid by satisfactory conversion ration, depending on the concentration of the substrate and amount of enzymes present in the reaction medium. The reaction may be carried out batch-wise or continuously.

According to another embodiment of the present process, a substrate α-ketocarboxylic acid is converted to a product, i.e., corresponding L-amino acid, in the presence of a growing culture such as a medium containing living cells, living cells separated from cultured broth, cells treated to an extent wherein an enzyme system necessary for the conversion of α-ketocarboxylic acid to L-amino acid is not destroyed, and in the presence of an energy source, without the artifical addition of NADH, NAD+ and the NADH regeneration system. The energy source is added in a reaction medium. The energy sources may act as an electron donor for reductive amination of α-ketocarboxylate. The energy sources include, for example, sugars such as arabinose, ribose, ribulose, xylose, fucose, rhamnose, fructose, galactose, gluconate, trehalose, glucose, mannitol, mannose, sorbitol, sorbose, inositol, lactose, maltose, sucrose, raffinose, glycerine, starches, inulin, glycogen, carboxymethylcellulose, and the like. Moreover, the energy sources include alcohols such as ethanol and methanol, organic acids such as propionic acid, acetic acid, formic acid, citric acid, pyruvic acid, succinic acid, malic acid, α-keto-glutaric acid, and the like.

For the second embodiment, the reaction medium, reaction pH, reaction temperature, and other conditions are selected as described for the first embodiment. The second embodiment also does not require the aerobic condition.

L-amino acid thus formed is recovered and purified according to any conventional procedure. For example, the reaction mixture is added with trichloroacetic acid to precipitate protein and the precipitate, if any, as well as the cells, is eliminated by filtration or centrifugation to obtain a filtrate or supernatant containing the product L-amino acid. The product in the filtrate or supernatant is then purified by, for example, ion exchange resin, and finally crystallized.

A quantitative analysis of L-amino acids is carried out by bioassay using, for example, *Leuconostoc mesenteroides* ATCC 8042, or by paper chromatography wherein a sample containing L-amino acid is separated in filter paper, a spot of L-amino acid is developed with ninhydrin, and the developed spot is eluted for spectrophotometric analysis.

EXAMPLES

The present invention will now be further illustrated by, but is by no means limited to, the following examples.

Example 1

Purification of L-Phenylalanine Dehydrogenase from Sporosarcina urea SCRC-R04

30 $l$ of a medium containing 0.2% L-phenylalanine, 0.5% yeast extract, 1.0% peptone, 0.2% $H_2HPO_4$, 0.1% NaCl and 0.02% $MgSO_4 \cdot 7H_2O$ (pH 7.0) was sterilized at 120° C. for 15 minutes, and after cooling, inoculated with Sporosarcina ureae SCRC-R04 (FERM P-8178, FERM BP-1012), and culturing was carried out aerobically at 30° C. for 24 hours. After the culturing, the cultured broth was centrifuged to obtain about 380 g of wet cells. The cells were washed once with 0.85% saline, and suspended in 1 $l$ of phosphate buffer (pH 7.0) containing 0.1 mM EDTA and 5 mM 2-mercaptoethanol, and the suspension was subjected to ultrasonic treatment at 9 KHz for 10 hours to disrupt the cells. The treated mixture was centrifuged at 14,000 X g for 20 minutes to obtain a crude cell-free extract containing L-phenylalanine dehydrogenase without cell debris. The cell-free extract was added with 5% protamine sulfate to an amount of 0.1 g protamine sulfate per 1 g protein, and stirred for 30 minutes to form a precipitate. The mixture containing the precipitate was centrifuged at 14,000 X g for 20 minutes to eliminate the precipitate. The supernatant containing the enzyme was dialyzed against 0.01M phosphate buffer (pH 7.0) containing 0.1M EDTA and 5 mM 2-mercaptoethanol. To 1990 ml of the dialyzate, 412 g of solid ammonium sulfate was added to achieve 30%-saturation. The salting-out mixture was stirred for 30 minutes and centrifuged at 14,000 X g for b 20 minutes to obtain 2100 ml of supernatant. The supernatant was added with 416 g of solid ammonium sulfate to achieve 60%-saturation. The salting-out mixture was centrifuged at 14,000 X g for 20 minutes to obtain a precipitate with enzyme activity, which precipitate was then dissolved in a small amount of 0.01M phosphate buffer (pH 7.0), and the solution was dialyzed against 0.1M phosphate buffer (pH 7.0) containing 0.1 mM EDTA and 5 mM 2-mercaptoethanol. The dialyzate was applied to a DEAE-Toyopearl 650M column previously equilibrated with a 0.01M phosphate buffer (pH 7.0) containing 0.1 mM EDTA and 5 mM 2-mercaptoethanol, and the column was eluted with 0.1M phosphate buffer (pH 7.0) containing 0.1 mM EDTA and 5 mM 2-mercaptoethanol to obtain active fractions.

These active fractions were combined and the combined active fraction was dialyzed against 0.01M phosphate buffer containing 0.1 mM EDTA and 5 mM 2-mercaptoethanol, and the dialyzate was applied to a hydroxyapatite column previously equilibrated with the same buffer. The adsorbed enzyme was eluted by linear gradient elution using from 0.01M to 0.15M phosphate buffer (pH 7.0) containing 0.1 mM EDTA and 5 mM 2-mercaptoethanol. The combined active fraction was gel-filtrated through a Sephadex G-200 column equilibrated with 0.5M phosphate buffer (pH 7.0) containing 0.1 mM EDTA, 5 mM 2-mercaptoethanol and 0.1M NaCl. The enzyme solution thus obtained was concentrated by ultrafiltration, and the concentrated enzyme solution was added with ammonium sulfate to crystallize the enzyme L-phenylalanine dehydrogenase. A micrograph of the crystals is set forth in FIG. 12. The purification steps from the cell-free extract to the final crystallization are set forth in Table 8.

ture was centrifuged at 14,000 X g for 20 minutes to obtain a precipitate with enzyme activity, which precipitate was then dissolved in a small amount of 0.01M phosphate buffer (pH 7.0), and the solution was dialyzed against 0.01M phosphate buffer (pH 7.0) containing 0.1 mM EDTA and 5 mM 2-mercaptoethanol. The dialyzate was applied to a DEAE-Toyoearl 650M column previously equilibrated with 0.01M phosphate buffer (pH 7.0) containing 0.1 m M EDTA and 5 mM 2-mercaptoethanol, and the column was eluted with 0.1M phosphate buffer (pH 7.0) containing 0.1 mM

TABLE 8

| Purification step | Total activity (Units) | Total protein (mg) | Specific activity (Units/mg) | Yield (%) |
|---|---|---|---|---|
| 1. Cell-free extract | 1,780 | 28,000 | 0.064 | 100 |
| 2. After protamine sulfate treatment | 1,920 | 24,000 | 0.080 | 108 |
| 3. Ammonium sulfate salting-out fraction (30–60% saturation) | 1,930 | 8,700 | 0.220 | 108 |
| 4. After DEAE-Toyopearl column | 1,560 | 400 | 3.9 | 88 |
| 5. After hydroxyapatite column | 1,080 | 50 | 21.6 | 61 |
| 6. After Sephadex G-200 column | 930 | 12 | 77.8 | 52 |
| 7. Crystal | 550 | 6.3 | 87.3 | 31 |

Example 2

Purification of L-Phenylalanine Dehydrogenase from Bacillus sp. SCRC-R79a (1)

10 l of medium containing 0.2% L-phenylalanine, 0.5% yeast extract, 1.0% peptone, 0.2% $H_2HPO_4$, 0.1% NaCl, and 0.2% $MgSO_4 \cdot 7H_2O$ (pH 7.0) was sterilized at 120° C. for 15 minutes, and after cooling, inoculated with Bacillus sp. SCRC-R79a (FERM P-8179, FERM BP-1013), and culturing was carried out aerobically at 30° C. for 24 hours. After the culturing, 10 l of the cultured broth was centrifuged to obtain about 108 g of wet cells. The cells were washed once with 0.85% saline, and suspended in 0.4 l of phosphate buffer (pH 7.0) containing 0.1 mM EDTA and 5 mM 2-mercaptoethanol, and the suspension was subjected to ultrasonic treatment at 9 KHz for 6 hours to disrupt the cells. The treated mixture was centrifuged at 14,000 X g for 20 minutes to obtain a crude cell-free extract containing L-phenylalanine dehydrogenase without cell debris.

The cell-free extract was added with 5% protamine sulfate to an amount of 0.1 g protamine sulfate per 1 g protein, and stirred for 30 minutes to form a precipitate. The mixture containing the precipitate was centrifuged at 14,000 X g for 20 minutes to eliminate the precipitate. The supernatant containing the enzyme was dialyzed against 0.01M phosphate buffer (pH 7.0) containing 0.1M EDTA and 5 mM 2-mercaptoethanol. To 400 ml of the dialyzate, 70.4 g of solid ammonium sulfate was added to achieve 30%-saturation. The salting-out mixture was stirred for 30 minutes and centrifuged at 14,000 X g for 20 minutes to obtain 430 ml of supernatant. The supernatant was added with 85.6 g of solid ammonium sulfate to achieve 60%-saturation. The salting out mix- EDTA and 5 mA 2-mercaptoethanol to obtain active fractions.

These active fractions were combined and the combined active fraction was dialyzed against 0.01M phosphate buffer (pH 7.0) containing 0.1 mM EDTA and 5 mM 2-mercaptoethanol, and the dialyzate was applied to a hydroxyapatite column previously equilibrated with the same buffer. The adsorbed enzyme was eluted by linear gradient elution using from 0.01M to 0.4M phosphate buffer (pH 7.0) containing 0.1 mM EDTA and 5 mM 2-mercaptoethanol. The combined active fraction was gel-filtrated through a Sephadex G-200 column equilibrated with 0.05M phosphate buffer (pH 7.0) containing 0.1 mM EDTA, 5 mM 2-mercaptoethanol and 0.1M NaCl. In this way, L-phenylalanine dehydrogenase was purified about 1800 times and obtained in a yield of about 60%. The purification steps are set forth in Table 9. The enzyme was verified to be homogeneous by polyacrylamide gel electrophoresis and SDS-polyacrylamide gel electrophoresis.

TABLE 9

| Purification step | Total activity (Units) | Total protein (mg) | Specific activity (Units/mg) | Yield (%) |
|---|---|---|---|---|
| 1. Cell-free extract | 600 | 8900 | 0.067 | 100 |
| 2. After protamine sulfate treatment | 490 | 6200 | 0.079 | 82 |
| 3. Ammonium sulfate salting-out fraction (30–60% saturation) | 470 | 5800 | 0.081 | 78 |
| 4. After DEAE-Toyopearl column | 380 | 470 | 0.81 | 63 |
| 5. After hydroxyapatite column | 370 | 17 | 22 | 62 |
| 6. After Sephadex G-200 column | 360 | 3 | 120 | 60 |

EXAMPLE 3

Purification of L-Phenylalanine Dehydrogenase from Bacillus sp. SCRC-R79a (2)

100 l of a medium containing 0.2% L-phenylalanine, 0.5% yeast extract, 1.0% peptone, 0.2% $H_2HPO_4$, 0.1% NaCl and 0.02% $MgSO_4 \cdot 7H_2O$ (pH 7.0) was sterilized at 120° C. for 15 minutes, acid after cooling, inoculated with Bacillus sp. SCRC-R79a (FERM P-8179, FERM BP-1013), and culturing was carried out aerobically at 30° C. for 22 hours. After the culturing, 100 l of the cultured broth was centrifuged to obtain about 0.7 kg of wet cells. The cells were suspended in about 4 l of 0.1M phosphate buffer (pH 7.9) containing 0.1 mM EDTA and 5 mM 2-mercaptoethanol, and the suspension was subjected to ultrasonic treatment at 9 KHz for 41 hours to disrupt the cells. The treated mixture was centrifuged at 14,000 X g for 20 minutes to obtain a crude cell-free extract containing L-phenylalanine dehydrogenase without cell debris. The cell-free extract was heated at 50° C. for 10 minutes, and immediately cooled on ice. To 3850 ml of the treated enzyme solution, 678 g of solid ammonium sulfate was added to achieve 30%-saturation. The salting out-mixture was stirred for 30 minutes and centrifuged at 14,000 X g for 20 minutes to obtain 3,400 ml of supernatant. The supernatant was added with 673 g of solid ammonium sulfate to achieve 60%-saturation. The salting out mixture was centrifuged at 14,000 X g for 20 minutes to obtain a precipitate with enzyme activity, which precipitate was then dissolved in a small amount of 0.01M phosphate buffer (pH 7.9), and the solution was dialyzed against 0.01M phosphate buffer (pH 7.9) containing 0.1 mM EDTA and 5 mM 2-mercaptoethanol. The dialyzate was applied to a DEAE-Toyopearl 650M column previously equilibrated with 0.01M phosphate buffer (pH 7.9) containing 0.1 mM EDTA and 5 mM 2-mercaptoethanol, and the column was eluted with 0.1M phosphate buffer (pH 7.9) containing 0.1 mM EDTA, 5 mM 2-mercaptoethanol, and 0.1M NaCl to obtain active fractions.

These active fractions were combined and the combined active fraction was dialyzed against a 0.01M phosphate buffer (pH 7.9) containing 0.1 mM EDTA and 5 mM 2-mercaptoethanol, and the dialyzate was applied to the second DEAE-Toyopearl 650M column previously equilibrated with the same buffer. The adsorbed enzyme was then eluted with the buffer, as in the previous state, to obtain active fractions. These active fractions were combined and the combined active fraction was dialyzed against a 0.01M phosphate buffer (pH 7.9) containing 1.0 mM EDTA and 5 mM 2-mercaptoethanol, and the dialyzate was applied to a hydroxyapatite column previously equilibrated with the same buffer. The adsorbed enzyme was eluted by linear gradient elution using from 0.01M to 0.4M phosphate buffer (pH 7.9) containing 0.1 mM EDTA and 5 mM 2-mercaptoethanol. The combined active fraction was concentrated, and the concentrate was gel-filtrated through a Sephadex G-200 column equilibrated with 0.05M phosphate buffer (pH 7.9) containing 0.1 mM EDTA, 5 mM 2-mercaptoethanol and 0.1M NaCl. In this way, L-phenylalanine dehydrogenase was purified about 1400 times, and obtained in a yield of about 54%. The enzyme solution thus obtained was concentrated by ultrafiltration, and the concentrated enzyme solution was added with ammonium sulfate to crystallize the enzyme L-phenylalanine dehydrogenase. A micrograph of the crystals is shown in FIG. 19. The purification steps from the cell-free extract to the final crystallization are set forth in Table 10.

TABLE 10

| Purification steps | Total activity (Units) | Total protein (mg) | Specific activity (Units/mg) | Yield (%) |
|---|---|---|---|---|
| 1. Cell-free extract | 4,410 | 63,300 | 0.0697 | 100 |
| 2. After heat treatment and salting-out with ammonium sulfate | 5,710 | 23,600 | 0.242 | 129 |
| 3. After the first DEAE-Toyopearl column | 4,210 | 1,180 | 3.57 | 95 |
| 4. After the second DEAE-Toyopearl column | 3,610 | 482 | 7.49 | 82 |
| 5. After hydroxyapatite column | 3,040 | 76.5 | 39.8 | 69 |
| 6. After Sephadex G-200 column | 2,420 | 25.3 | 94.9 | 54 |

Example 4

Production of L-phenylalanine using L-Phenylalanine Dehydrogenase-Crude Preparation from Sporosarcina ureae SCRC-R04

300 ml of a reaction mixture containing 5 g (22 m moles) of sodium phenylpyruvate, 3 g (49 m moles) of ammonium formate, 0.21 g (0.29 m moles) of NAD+ 18 m moles of Tris-HCl buffer (pH 8.5), 43.2 units of L-phenylalanine dehydrogenase (as a crude preparation corresponding to the ammonium sulfate fraction at the third step in Table 8 in Example 1), and 49.0 units of formate dehydrogenase (as a crude preparation partially purified from Candida boidinii No. 2201, pH 8.5) was incubated at 30° C. for 24 hours. The amount of L-phenylalanine formed in the reaction medium was determined to be 1.91 g (11.6 m moles, 52.7% yield) according to a bioassay using Leuconostoc mesenteroides.

The reaction mixture was added with 30 ml of 20% trichloroacetic acid aqueous solution, and centrifuged to eliminate protein. The supernatant was applied to a cation exchanger Amberlite IR-120 (H+ form) column, and the column was eluted with 1M aqueous ammonia to obtain L-phenylalanine-containing fractions. These fractions were combined and the combined fraction was concentrated, and the concentrate was applied to an anion exchanger Amberlite IRA-400 (OH− form) column, and the column was eluted with 1M formic acid to obtain L-phenylalanine-containing fractions, which were combined and concentrated to dryness. The residue was dissolved in a small amount of warm water, and the solution was added with ethanol to a 50% ethanol concentration, and allowed to crystallize L-phenylalanine 4° C. The crystal was recrystallized in the same manner to obtain 0.458 g of water-white solid. An elemental analysis of the preparation thus obtained provided the following results.

| | Found (%) | Calculated (%) |
|---|---|---|
| C | 65.33 | 65.43 |
| H | 6.61 | 6.71 |
| N | 8.48 | 8.48 |

Melting point=270° C. (decomposition). $[\alpha]_D^{25} = -35.5°$ (c=0.48, $H_2O$), L-form, optically pure. Mass spectrum, NMR spectrum, and IR spectrum show the product is L-phenylalanine.

Example 5

High Concentration Synthesis of L-Phenylalanine using L-Phenylalanine Dehydrogenase—Partially Purified Preparation from Sporosarcina ureae SCRC-R04

5 ml of a reaction mixture containing 3.57 m moles of sodium phenylpyruvate, 100 μ moles of NAD+, 5 m moles of NH₄Cl, 272 μ moles of Tris-HCl buffer (pH 8.5), 7.84 m moles of sodium formate, 35 units of L-phenylalanine dehydrogenase (as a partially purified preparation treated with the DEAE-Toyopearl column at the fourth step in Table 8, in Example 1), and 10.2 units of formate dehydrogenase (as a preparation partially purified from *Candida boidinni* No. 2201, pH 8.5) was incubated at 30° C. for 24 hours.

A bioassay of the reaction mixtured showed the formation of 580 mg (3.51 m moles, 98.5% yield) of L-phenylalanine.

Example 6

Production of L-Phenylalanine using L-Phenylalanine Dehydrogenase-Crude Preparation from Sporosarcina ureae SCRC-R04

13.0 ml of a reaction mixture containing 200 μ moles of sodium phenylpyruvate, 20 μ moles of NAD+, 200 μ moles of sodium formate, 600 μ moles of Tris-HCl buffer (pH 8.5), 11.9 units of formate dehydrogenase (as a cell-free extract from *Candida boidinii*, pH 8.5), and 13.2 units of L-phenylalanine dehydrogenase (as a crude enzyme fraction precipitated within 30 to 60% ammonium sulfate saturation at the third step in Table 8 in Example 1) was incubated at 30° C. for 15 hours. A bioassay of the reaction mixture showed the formation of 32.8 mg (198.8 μ moles, 98.4% yield) of L-phenylalanine.

Example 7

Production of L-Phenylalanine Using L-Phenylalanine Dehydrogenase-Partially Purified Preparation from *Bacillus sp.* SCRC-R79a 5.0 ml of a reaction mixture containing 400 μ moles of sodium phenylpyruvate, 800 μ moles of ammonium formate, 5 μ moles of NAD+, 260 μ moles of Tris-HCl buffer (pH 8.5), 0.5 units of formate dehydrogenase (as a crude preparation, pH 8.5), and 0.25 units of L-phenylalanine dehydrogenase (as an enzyme preparation pufified from *Bacillus sp.* SCRC-R79a by protamine treatment of cell-free extract, ammonium sulfate fractionation, DEAE-Toyopearl chromatography and hydroxyapatite chromatography) was incubated at 30° C. for 24 hours. A bioassay of the reaction mixture showed the formation of 64.4 mg (390.0 μ moles, 97.5% yield) of L-phenylalanine. L-phenylalanine was recovered according to a procedure described in Example 3.

Example 8

Production of L-Phenylalanine Using L-Phenylalanine Dehydrogenase-Partially purified Preparation from *Bacillus sp.* SCRC-R79a To 50 ml of a reaction mixture containing 0.91 g (4 m moles) of sodium phenylpyruvate, 0.75 g (11.9 m moles) of ammonium formate, 36 mg (50 μ moles) of NAD+ and 2.5 m moles of Tris-HCl buffer (pH 8.5), a cellulose tube containing 20 units of L-phenylalanine dehydrogenase (a fraction after DEAE-Toyopearl column chromatography), and 15 units of formate dehydrogenase (a preparation partially purified from *Candida boidinii* No. 2201, pH 8.5) was inserted, and the whole was incubated at 30° C. for 24 hours. After the reaction, the cellulose tube was removed from the reaction mixture and inserted to a fresh reaction mixture having the same composition as described above, and the whole was incubated as described above. This procedure was repeated 28 times, i.e., the same enzyme preparations were repeatedly used for 28 batches of the reaction. A bioassay of each reaction mixture showed the formation of 11.74 g (65 m moles, 58% yield), in total, of L-phenylalanine. A portion of the reaction mixture (450 ml containing 3.58 g of L-phenylalanine) was applied to a cation exchanger Amberlite IR-120 (H+ form) column, and the column was eluted with 1M aqueous ammonia to obtain L-phenylalanine-containing fractions. The fractions were combined and concentrated, and the concentrate was applied to an anion exchanger Amberlite IRA-400 (OH⁻ form) column, and the column was eluted with 1M formic acid to obtain L-phenylalanine-containing fractions. The fractions were combined and concentrated to dryness. The residue was dissolved in a small amount of warm water, and the solution was allowed to crystallize L-phenylalanine at 4° C. The crystal was recrystallized in the same manner to obtain 1.235 g of water-white solid.

An elemental analysis of the preparation thus obtained provided the following results.

|   | Found (%) | Calculated (%) |
|---|---|---|
| C | 65.48 | 65.44 |
| H | 6.65 | 6.71 |
| N | 8.47 | 8.48 |

Melting point=252−254° C. (decomposition). $[\alpha]_D^{20} = -34.1°$ (c=1.72, H₂O), L-form, optical purity=98.% e.e., Mass spectrum, NMR spectrum, and IR spectrum showed that the product is L-phenylalanine.

Example 9

High Concentration Synthesis of L-Phenylalanine Using L-Phenylalanine Dehydrogenase-Partially Purified Preparation from *Bacillus sp.* SCRC-R79a 10 ml of a reaction mixture consisting 1.8 g (8 m moles) of sodium phenylpyruvate, 0.98 g (15.54 m moles) of ammonium formate, 72 mg (100 μ moles) of NAD+, 5 m moles of Tris-HCl buffer (pH 8.5), 40 units of L-phenylalanine dehydrogenase (as a preparation after DEAE-Toyopearl column chromatography), and 20 units of formate dehydrogenase (as a preparation partially purified from *Candida boidinii*, pH 8.5) was incubated at 30° C. for 24 hours. A bioassay of the reaction medium showed the formation of 1.12 g (6.78 m moles, 86% yield) of L-phenylalanine.

Example 10

Production of L-Phenylalanine Using L-Phenylalanine Dehydrogenase-Crude Preparation from *Bacillus sp.* SCRC-R79a 5 ml of a reaction mixture containing 400 μ moles of sodium phenylpyruvate, 1.2 m moles of ammonium chloride, 480 μ moles of NADH, 250 μ moles of Tris-HCl buffer (pH 8.5), and 2.0 units of L-phenylalanine dehydrogenase (as a crude enzyme preparation precipitated between 30–60% ammonium sulfate saturation after heat-treatment at 50° C. for 10 minutes of the cell-free extract from cultured cells of *Bacillus sp.* SCRC-R79a, corresponding to the second step in Table 10 in Example 3) was incubated at 30° C. for 24 hours. A bioassay of the reaction mixture showed the formation of 63.5 mg (384 μ moles, 96.8% yield) of L-phenylalanine.

Example 11

Preparation of L-Phenylalanine Using L-Phenylalanine Dehydrogenase-Crude Preparation from *Bacillus sp.* SCRC-R79a 5 ml of a reaction mixture containing 400 μ moles of sodium phenylpyruvate, 1.2 m moles of ammonium formate, 2.5 μ moles of NAD+, 250 μ moles of Tris-HCl buffer (pH 8.5), 1.5 units of formate dehydrogenase (as a preparation partially purified from *Candida boidinii* No. 2201, pH 8.5), and 2.0 units of L-phenylalanine dehydrogenase (as a crude enzyme preparation precipitated between 30%–60% ammonium sulfate saturation after heat-treatment at 50° C. for 10 minutes of the cell-free extract from cultured cells of *Bacillus sp.* SCRC-R79a, corresponding to the second step in Table 10 in Example 3) was incubated at 30° C. for 24 hours. A bioassay of the reaction mixture showed the formation of 62.8 mg (380 μ moles, 95.0% yield) of L-phenylalanine.

Example 12

Production of L-Phenylalanine Using L-Phenylalanine Dehydrogenase-Crude Preparation from *Bacillus sp.* SCRC-R53b 5 ml of a reaction mixture containing 400 μ moles of sodium phenylpyruvate, 1.2 m moles of ammonium formate, 2.5 μ moles of NAD+, 250 μ moles of Tris-HCl buffer (pH 8.5), 1.5 units of formate dehydrogenase (as a preparation partially purified from *Candida boidinii* No. 2201, pH 8.5), and 2.0 units of L-phenylalanine dehydrogenase (as a preparation precipitated between 30%–60% ammonium sulfate saturation after heat-treatment at 50° C. for 10 minutes of a cell-free extract from cultured cells of *Bacillus sp.* SCRC-R53b) was incubated at 30° C. for 20 hours.

A bioassay of the reaction mixture showed the formation of 573 mg (347 μ moles, 86.8% yield) of L-phenylalanine.

Example 13

Production of L-Phenylalanine Using L-Phenylalanine Dehydrogenase-Crude Preparation from *Bacillus sp.* SCRC-101A 5 ml of a reaction mixture containing 400 μ moles of sodium phenylpyruvate, 1.2 m moles of ammonium formate, 2.5 μ moles of NAD+, 250 μ moles of Tris-HCl buffer (pH 8.5, 1.5 units of formate dehydrogenase (as a preparation partially purified from *Candida boidinii* No. 2201, pH 8.5), and 2.0 units of L-phenylalanine dehydrogenase (as a preparation precipitated between 30%–60% ammonium sulfate saturation after heat-treatment at 50° C. for 10 minutes of a cell-free extract of cultured cells of *Bacillus sp.* SCRC-101A) was incubated at 30° C. for 20 hours.

A bioassay of the reaction mixture showed the formation of 58.3 mg (353 μ moles, 88.3% yield) of L-phenylalanine.

Example 14

Production of L-Phenylalanine Using L-Phenylalanine Dehydrogenase-Crude Preparation from *Bacillus sp.* SCRC-114D 5 ml of a reactive mixture containing 400 μ moles of sodium phenylpyruvate, 1.2 m moles of ammonium formate, 2.5 μ moles of NAD+, 250 μ moles of Tris-HCl buffer (pH 8.5), 1.5 units of formate dehydrogenase (as a preparation partially purified from *Candida boidinii* No. 2201, pH 8.5), and 2.0 units of L-phenylalanine dehydrogenase (as a preparation precipitated between 30%–60% ammonium sulfate saturation from a cell-free extract of cultured cells of *Bacillus sp.* SCRC-114D) was incubated at 30° C. for 20 hours.

A bioassay of the reaction mixture showed the formation of 52.5 mg (318 μ moles, 79.5% yield) of L-phenylalanine.

Example 15

Production of L-Tyrosine Using L-Phenylalanine Dehydrogenase-Partially Purified Preparation from *Bacillus sp.* SCRC-R79a 300 ml of a reaction mixture containing 1.1 g (6 m moles) of 4-hydroxyphenylpyruvic acid, 4.5 g (3.13 m moles) of ammonium formate, 216 mg (300 μ moles) of NAD+, 15 m moles of Tris-HCl buffer (pH 8.5), 24 units of L-phenylalanine dehydrogenase (as a preparation after DEAE-Toyopearl column chromatography), and 30 units of formate dehydrogenase (as a crude preparation purified from *Candida boidinii* No. 2201, pH 8.5) was incubated at 30° C. for 45 hours. During the incubation, L-tyrosin crystallized.

An elemental analysis of the crystal provided the following results.

|   | Found (%) | Calculated (%) |
|---|---|---|
| C | 59.45 | 59.66 |
| H | 6.11 | 6.12 |
| N | 7.69 | 7.73 |

$[\alpha]_D^{25} = -7.33°$ (c=4, 6N HCl), L-form, optical purity=100% e.e., Mass spectrum, NMR spectrum, and IR spectrum showed that the product is L-tyrosine.

Example 16

General procedure

Various kinds of α-ketocarboxylic acids listed in Tables 11 to 15 were converted to corresponding L-amino acids. In Tables 11 to 15, relating to L-phenylalanine dehydrogenase preparation "crude enzyme" means a preparation prepared by ammonium sulfate fractionation of a cell-free extract, and "partially purified enzyme" means an enzyme preparation treated with DEAE-Toyopearl column. NAD+ or NADH was added to 1 to 20 mM of the final concentration. Ammonium ion was supplied in a form of ammonium chloride, ammonium formate or $NH_4OH-NH_4Cl$ buffer (pH 9.0) to 0.05M to 0.5M of the final concentration. Formate was supplied in a form of sodium formate or ammonium formate to an amount of 1 to 30 equivalents relating to a α-ketocarboxylic acid. pH of the reaction mixture was adjusted to 8.5 to 9 by using Tris-HCl buffer (pH 8.5) or $NH_4OH-NH_4Cl$ buffer (pH 9.0) to a concentration of 0.05M to 0.5M. Reaction was carried out at 30° C.

Particular reaction condition

Reaction No. 1

50 ml of a reaction mixture containing 0.61 g (3 m moles) of sodium phenylpyruvate, 0.54 g (3 m moles) of D-fructose, and cells of *Sporosarcina ureae* SCRC-R04 (prepared by centrifuging 200 ml of cultured broth to obtain cells, and once washing the cells with physiological saline) was allowed to stand at 30° C. for 28 hours. A bioassay of the reaction mixture showed the formation of 0.34 g (2.07 m moles, 69% yield) of L-phenylalanine.

A similar reaction condition was applied to reactions Nos. 2, 8, 30, 33, and 34.

Reaction No. 3

5 ml of a reaction mixture containing 20.4 mg (100 μ moles) of sodium phenylpyruvate, 2.5 μ moles of $NAD^+$, 250 μ moles of Tris-HCl buffer (8.5), 2 m moles of ammonium formate 5 mg of dried cells of *Candida boidinii*, wet cells of *Sporosarcina ureae* SCRC-R04 (washed cells obtained from 25 ml of cultured borth) was incubated at 30° C. for 24 hours. A bioassay of the reaction mixture showed the formation of 11.7 mg (71 μ moles, 71% yield) of L-phenylalanine.

A similar reaction condition was applied to reactions Nos. 9 and 21.

Reaction No. 5

5 ml of a reaction mixture containing 17.02 mg (100 μ moles) of sodium α-keto-γ-methylthiobutyrate, 76.3 mg (100 μ moles) of NADH, 250 μ moles of Tris-HCl buffer (pH 8.5), 107 mg (2 m moles) of ammonium chloride, 0.5 units of L-phenylalanine dehydrogenase (a fraction precipitated between 30%-60% ammonium sulfate saturation) was incubated at 30° C. for 24 hours. A bioassay of the reaction mixture showed the formation of 10.02 mg (67 μ moles) of L-methionine.

A similar reaction condition was applied to reactions Nos. 16, 35, 37.

Reaction No. 7

5 ml of a reaction mixture containing 17.02 mg (100 μ moles) of sodium α-keto-γ-methylthiobutyrate, 50 mg (800 μ moles) of ammonium formate, 3.6 mg (5 μ moles) of $NAD^+$, 250 μ moles of Tris-HCL buffer (pH 8.5), 2.5 units of L-phenylalanine dehydrogenase (a homogeneously purified enzyme preparation derived from *Sporosarcina ureae* SCRC-R04), and 0.5 units of formate dehydrogenase (a preparation partially purified from *Candida boidinii* No. 2201) was incubated at 30° C. for 24 hours. A bioassay of the reaction mixture showed the formation of 13.05 mg (87 μ moles) of L-methionine.

A similar reaction condition was applied to reactions Nos. 4, 6, 10, 11, 12, 13, 14, 15, 17, 18, 19, 20, 22, 23, 24, 25, 26, 27, 28, 29, 31, 32, 36, 38, 39, 40.

From the reaction mixture of reaction No. 15, L-tyrosine was isolated as a crystal. An elemental analysis of the crystal provided the following results:

|   | Found (%) | Calculated (%) |
|---|-----------|----------------|
| C | 59.45     | 59.66          |
| H | 6.11      | 6.12           |
| N | 7.69      | 7.73           |

$[\alpha]_D^{25} = -7.33°$ (c=4, 6N HCl), L-form, optical purity=100% e.e., Mass spectrum, NMR spectrum, and IR spectrum showed that the product is L-tyrosine.

From the reaction mixture of reaction No. 26, 4-vinyl-L-phenylalanine was isolated as a crystal. An elemental analysis of the crystal showed the following results:

|   | Found (%) | Calculated (%) |
|---|-----------|----------------|
| C | 69.01     | 69.09          |
| H | 6.79      | 6.87           |
| N | 7.29      | 7.32           |

Melting point=190° C. (decomposition). $\alpha[_D^{20}] = -13.53$ (c=1.02, 4N NaOH). Mass spectrum, NMR spectrum, and IR spectrum showed that the product is 4-vinyl-L-phenylalanine.

From the reaction mixture of reaction No. 27, 4-fluoro-L-phenylalanine was isolated as a crystal. An elemental analysis of the crystal provided the following results:

|   | Found (%) | Calculated (%) |
|---|-----------|----------------|
| C | 58.92     | 59.01          |
| H | 5.47      | 5.50           |
| N | 7.64      | 7.65           |

Melting point =223° C. to 226° C. $[\alpha]_D^{20} = -1.12$ (c=0.83, 4N NaOH). Mass spectrum, NMR spectrum, and IR spectrum showed that the product is 4-fluoro-L-phenylalanine.

Other L-amino acids produced were analyzed by bioassay.

Results are summarized in Tables 11 to 15.

TABLE 11

Production of L-Amino Acid Using Sporosarcina ureac SCRC-R04

| Reaction No. | α-ketocarboxylic acid | Amount of α-ketocarboxylate (μmol) | Reaction volume (ml) | L-Phenylalanine dehydrogenase Preparation form | Units | Co-enzyme | NADH Regeneration system Preparation form | Units | Reaction time (hr) | Product | Yield (%) |
|---|---|---|---|---|---|---|---|---|---|---|---|
| 1 | Sodium phenylpyruvate | 3,000 | 50 | Washed cells from 200 ml cultured broth | — | | Contained in cells. 3,000 μmoles fructose added as electron donor | | 28 | L-Phenylalanine | 69 |
| 2 | Sodium phenylpyruvate | 2,400 | 20 | Washed cells from 600 ml cultured broth | — | | Contained in cells. 2,400 μmoles fructose added as electron donor | | 7 | L-Phenylalanine | 56 |
| 3 | Sodium phenylpyruvate | 100 | 5 | Washed cells from 25 ml cultured | — | $NAD^+$ | Dried cells of *C. boidinii* 5 mg | | 24 | L-Phenylalanine | 71 |

TABLE 11-continued

Production of L-Amino Acid Using Sporosarcina ureac SCRC-R04

| Reaction No. | α-ketocarboxylic acid | Amount of α-ketocar-boxylate (μmol) | Reaction volume (ml) | L-Phenylalanine dehydrogenase Preparation form | Units | Co-enzyme | NADH Regeneration system Preparation form | Units | Reaction time (hr) | Product | Yield (%) |
|---|---|---|---|---|---|---|---|---|---|---|---|
| 4 | 4-Hydroxyphenyl-pyruvic acid | 60 | 5 | broth Crude enzyme | 2.5 | NAD+ | Formate dehydrogenase | 0.5 | 24 | L-Tyrosine | 99 |
| 5 | Sodium α-keto-γ-methylthiobutyrate | 100 | 5 | Crude enzyme | 2.5 | NADH | Absent | Absent | 24 | L-Methionine | 67 |
| 6 | Sodium α-keto-γ-methylthiobutyrate | 100 | 5 | Crude enzyme | 2.5 | NAD+ | Formate dehydrogenase | 0.5 | 24 | L-Methionine | 69 |
| 7 | Sodium α-keto-γ-methylthiobutyrate | 100 | 5 | Homogeneously purified enzyme | 2.5 | NAD+ | Formate dehydrogenase | 0.5 | 24 | L-Methionine | 87 |
| 8 | Sodium α-keto-γ-methylthiobutyrate | 150 | 5 | Washed cells from 25 ml cultured broth | — | | Contained in cells. 300 μmoles fructose added as electron donor | | 24 | L-Methionine | 34 |
| 9 | Sodium α-keto-γ-methylthiobutyrate | 600 | 5 | Washed cells from 25 ml cultured broth | — | NAD+ | Dried cells of C. boidinii 5 mg | | 24 | L-Methionine | 30 |
| 10 | Sodium α-keto-isovalerate | 100 | 5 | Homogeneously purified enzyme | 2.5 | NAD+ | Formate dehydrogenase | 5 | 46 | L-Valine | 97 |
| 11 | Sodium DL-α-keto-β-methyl-n-valerate | 100 | 5 | Homogeneously purified enzyme | 2.5 | NAD+ | Formate dehydrogenase | 5 | 46 | L-Isoleucine | 48 |
| 12 | Sodium α-keto-isocaproate | 100 | 5 | Homogeneously purified enzyme | 2.5 | NAD+ | Formate dehydrogenase | 5 | 38 | L-Leucine | 83 |

TABLE 12

Production of L-Amino Acid Using Bacillus sp. SCRC-R79a

| Reaction No. | α-ketocarboxylate | Amount of α-ketocar-boxylate (μmol) | Reaction volume (ml) | L-Phenylalanine dehydrogenase Preparation form | Units | Co-enzyme | NADH Regeneration system Preparation form | Units | Reaction time (hr) | Product | Yield (%) |
|---|---|---|---|---|---|---|---|---|---|---|---|
| 13 | Sodium phenylpyruvate | 100 | 5 ml, containing 5% DMSO | Homogeneously purified enzyme | 0.5 | NAD+ | Formate dehydrogenase | 0.5 | 24 | L-Phenylalanine | 91 |
| 14 | Sodium phenylpyruvate | 100 | 5 ml, containing 5% acetonitrile | Homogeneously purified enzyme | 0.5 | NAD+ | Formate dehydrogenase | 0.5 | 24 | L-Phenylalanine | 98 |
| 15 | 4-Hydroxyphenyl-pyruvic acid | 6000 | 300 | Partially purified enzyme | 2.4 | NAD+ | Formate dehydrogenase | 30 | 45 | L-Tyrosine | 99 |
| 16 | 4-Hydroxyphenyl-pyruvic acid | 60 | 5 | Homogeneously purified enzyme | 0.5 | NADH | Absent | Absent | 24 | L-Tyrosine | 86 |
| 17 | 4-Hydroxyphenyl-pyruvic acid | 300 | 5 | Homogeneously purified enzyme | 5 | NAD+ | Formate dehydrogenase | 5 | 72 | L-Tyrosine | 79 |
| 18 | 4-Hydroxyphenyl-pyruvic acid | 60 | 5 | Homogeneously purified enzyme | 0.5 | NAD+ | Formate dehydrogenase | 0.5 | 24 | L-Tyrosine | 89 |
| 19 | 4-Hydroxyphenyl-pyruvic acid | 100 | 5 ml, containing 5% | Homogeneously purified enzyme | 0.5 | NAD+ | Formate dehydrogenase | 0.5 | 24 | L-Tyrosine | 86 |

TABLE 12-continued

Production of L-Amino Acid Using *Bacillus sp.* SCRC-R79a

| Reaction No. | α-ketocarboxylate | Amount of α-ketocarboxylate (μmol) | Reaction volume (ml) | L-Phenylalanine dehydrogenase Preparation form | Units | Co-enzyme | NADH Regeneration system Preparation form | Units | Reaction time (hr) | Product | Yield (%) |
|---|---|---|---|---|---|---|---|---|---|---|---|
| 20 | 4-Hydroxyphenyl-pyruvic acid | 100 | DMSO 5 ml, containing 5% acetonitrile | Homogeneously purified enzyme | 0.5 | NAD+ | Formate dehydrogenase | 0.5 | 24 | L-Tyrosine | 89 |
| 21 | 4-Hydroxyphenyl-pyruvic acid | 200 | 5 | Washed cells from 25 ml cultured broth | — | NAD+ | Dried cells of *C. boidinii* 5 mg | | 24 | L-Tyrosine | 41 |
| 22 | Sodium α-keto-γ-methylthiobutyrate | 100 | 5 | Homogeneously purified enzyme | 0.5 | NAD+ | Formate dehydrogenase | 0.5 | 24 | L-Methionine | 68 |
| 23 | Sodium α-keto-γ-methylthiobutyrate | 100 | 5 | Crude enzyme | 0.5 | NAD+ | Formate dehydrogenase | 0.5 | 24 | L-Methionine | 75 |
| 24 | Sodium α-keto-γ-methylthiobutyrate | 100 | 5 ml, containing 5% DMSO | Homogeneously purified enzyme | 0.5 | NAD+ | Formate dehydrogenase | 0.5 | 24 | L-Methionine | 86 |
| 25 | Sodium α-keto-γ-methylthiobutyrate | 100 | 5 ml, containing 5% acetonitrile | Homogeneously purified enzyme | 0.5 | NAD+ | Formate dehydrogenase | 0.5 | 24 | L-Methionine | 89 |
| 26 | 4-Vinylphenyl-pyruvic acid | 1020 | 50 | Partially purified enzyme | 100 | NAD+ | Formate dehydrogenase | 86 | 48 | 4-Vinyl-L-phenylalanine | 49 |
| 27 | 4-Fluorophenyl-pyruvic acid | 1100 | 30 | Partially purified enzyme | 10 | NAD+ | Formate dehydrogenase | 10 | 24 | 4-Fluoro-L-phenylalanine | 20 |

TABLE 13

Production of L-Amino Acid Using Bacillus sp. SCRC-R53b

| Reaction No. | α-ketocarboxylate | Amount of α-ketocarboxylate (μmol) | Reaction volume (ml) | L-Phenylalanine dehydrogenase Preparation form | Units | Co-enzyme | NADH Regeneration system Preparation form | Units | Reaction time (hr) | Product | Yield (%) |
|---|---|---|---|---|---|---|---|---|---|---|---|
| 28 | 4-Hydroxyphenyl-pyruvic acid | 60 | 5 | Crude enzyme | 0.5 | NAD+ | Formate dehydrogenase | 0.5 | 24 | L-Tyrosine | 92 |
| 29 | Sodium α-keto-γ-methylthiobutyrate | 100 | 5 | Crude enzyme | 0.5 | NAD+ | Formate dehydrogenase | 0.5 | 24 | L-Methionine | 71 |
| 30 | 4-Hydroxyphenyl-pyruvic acid | 150 | 5 | Washed cells from 25 ml cultured broth | — | | Contained in cells. 300 μmoles fructose added as electron donor | | 24 | L-Tyrosine | 31 |

TABLE 14

Production of α-Amino Acid Using Bacillus sp. SCRC-R101A

| Reaction No. | α-ketocarboxylate | Amount of α-ketocarboxylate (μmol) | Reaction volume (ml) | L-Phenylalanine dehydrogenase Preparation form | Units | Co-enzyme | NADH Regeneration system Preparation form | Units | Reaction time (hr) | Product | Yield (%) |
|---|---|---|---|---|---|---|---|---|---|---|---|
| 31 | 4-Hydroxyphenyl-pyruvic acid | 60 | 5 | Crude enzyme | 0.5 | NAD+ | Formate dehydrogenase | 0.5 | 24 | L-Tyrosine | 87 |
| 32 | Sodium α-keto-γ-methylthiobutyrate | 100 | 5 | Crude enzyme | 0.5 | NAD+ | Formate dehydrogenase | 0.5 | 24 | L-Methionine | 68 |

TABLE 15

Production of L-Amino Acid Using *Bacillus badius* IAM 11059

| Reaction No. | α-ketocarboxylate | Amount of α-ketocarboxylate (μmol) | Reaction volume (ml) | L-Phenylalanine dehydrogenase Preparation form | Units | Co-enzyme | NADH Regeneration system Preparation form | Units | Reaction time (hr) | Product | Yield (%) |
|---|---|---|---|---|---|---|---|---|---|---|---|
| 33 | Sodium phenylpyruvate | 364 | 5 | Washed cells from 5 ml cultured broth | — | Contained in cells. 300 μmoles glycerol added as electron donor | | | 24 | L-Phenylalanine | 42 |
| 34 | Sodium phenylpyruvate | 55 | 3 | Washed cells from 15 ml cultured broth | — | Contained in cells. 510 μmoles glycerol added as electron donor | | | 24 | L-Phenylalanine | 93 |
| 35 | Sodium phenylpyruvate | 100 | 5 | Crude enzyme | 0.5 | NADH | Absent | Absent | 24 | L-Phenylalanine | 95 |
| 36 | Sodium phenylpyruvate | 100 | 5 | Crude enzyme | 0.5 | NAD+ | Formate dehydrogenase | 0.5 | 24 | L-Phenylalanine | 95 |
| 37 | Sodium phenylpyruvate | 100 | 5 | Partially purified enzyme | 0.5 | NADH | Absent | Absent | 24 | L-Phenylalanine | 80 |
| 38 | Sodium phenylpyruvate | 100 | 5 | Partially purified enzyme | 0.5 | NAD+ | Formate dehydrogenase | 0.5 | 24 | L-Phenylalanine | 97 |
| 39 | 4-Hydroxyphenylpyruvic acid | 60 | 5 | Crude enzyme | 0.5 | NAD+ | Formate dehydrogenase | 0.5 | 24 | L-Tyrosine | 98 |
| 40 | Sodium α-keto-γ-methylthiobutyrate | 100 | 5 | Crude enzyme | 0.5 | NAD+ | Formate dehydrogenase | 0.5 | 24 | L-Methionine | 90 |

We claim:

1. An enzyme L-phenylalanine dehydrogenase characterized by:
   (1) catalyzing a reaction wherein L-phenylalanine, NAD+ and $H_2O$ react to form phenylpyruvate, NADH and ammonium ion, and a reverse reaction thereof;
   (2) having a molecular weight of about 290,000 as determined by high performance liquid chromatography and a molecular weight of about 305,000 as determined by a sedimentation equilibrium method, and exhibiting a sub-unit with a molecular weight of about 38,000 to 39,000 as determined by SDS-polyacrylamide gel electrophoresis; and
   (3) having a high specificity for L-phenylalanine and a very low specificity for L-tryptophan, L-tyrosine and L-methionine for oxidative deamination.

2. An enzyme L-phenylalanine dehydrogenase characterized by:
   (1) catalyzing a reaction wherein L-phenylalanine, NAD+ and $H_2O$ react to form phenylpyruvate, NADH, and ammonium ion, and a reverse reaction thereof; and
   (2) having a molecular weight of about 290,000 as determined by high performance liquid chromatography and a molecular weight of about 305,000 as determined by a sedimentation equilibrium method, and exhibiting a sub-unit with a molecular weight of about 38,000 to 39,000 as determined by SDS-polyacrylamide gel electrophoresis; and
   (3) being produced by a microorganism belonging to the genus Sporosarcina.

3. An enzyme L-phenylalanine dehydrogenase characterized by:
   (1) catalyzing a reaction wherein L-phenylalanine, NAD+, and $H_2O$ react to form phenylpyruvate, NADH and ammonium ion, and a reverse reaction thereof;
   (2) exhibiting a molecular weight of about 290,000 as determined by high performance liquid chromatography, a molecular weight of about 340,000 as determined by a sedimentation equilibrium method, and exhibiting a sub-unit with a molecular weight of about 38,000 to 39,000 as determined by SDS-polyacrylamide gel electrophoresis; and
   (3) having a high specificity for L-phenylalanine and L-tyrosine, and a very low specificity for L-tryptophan and L-methionine for oxidative deamination.

4. An enzyme L-phenylalanine dehydrogenase characterized by:
   (1) catalyzing a reaction wherein L-phenylalanine, NAD+ and $H_2O$ react to form phenylpyruvate, NADH and ammonium ion; and
   (2) exhibiting a molecular weight of about 290,000 as determined by high performance liquid chromatography, a molecular weight of about 340,000 as determined by a sedimentation equilibrium method, and exhibiting a sub-unit with a molecular weight of about 38,000 to 39,000 as determined by SDS-polyacrylamide gel electrophoresis; and
   (3) being produced by a microorganism belonging to the genus Bacillus.

5. A process for production of L-phenylalanine dehydrogenase characterized by:
   (1) culturing a microorganism belonging to the genus Sporosarcina and being capable of producing the L-phenylalanine dehydrogenase to form the L-phenylalanine dehydrogenase; and
   (2) recovering the L-phenylalanine dehydrogenase.

6. A process according to claim 5, wherein the *Sporosarcina urea* is selected from the group consisting of *Sporosarcina urea* SCRC-R04, FERM P-8178, FERM BP-1012; *Sporosarcina ureae* IFO 12698; and *Sporosarcina ureae* IFO 12699, ATCC 6473.

7. A process for production of L-phenylalanine dehydrogenase characterized by:
   (1) culturing a microorganism belonging to the genus Bacillus and capable of producing the L-phenylalanine dehydrogenase to form the L-phenylalanine dehydrogenase; and (2) recovering the L-phenylalanine dehydrogenase.

8. A process according to claim 7, wherein the microorganism is selected from the group consisting of *Bacillus alvei, Bacillus thiaminolyticus, Bacillus badius,* and *Bacillus sphaericus.*

9. A process according to claim 7, wherein the microorganism is selected from the group consisting of *Bacillus alvei* IFO 3343; *Bacillus thiaminolyticus* IAM 1034, FERM P-8528; *Bacillus badius* IAM 11059, FERM P-8529, ATCC 14574; *Bacillus sphaericus* IFO 12622; *Bacillus sphaericus* IAM 1228, FERM P-8527, *Bacillus sp.*SCRC-R79a, FERM P-8179, FERM BP-1013; and *Bacillus sp.* SCRC-114D, FERM BP-1011.

10. A biologically pure culture of microorganism capable of producing L-phenylalanine dehydrogenase, which is *Sporosarcina ureae* SCRC-R04, FERM P-8178, FERM BP-1012.

11. A biologically pure culture of microorganism capable of producing L-phenylalanine dehydrogenase, selected from the group consisting of *Bacillus sp.* SCRC-R79a FERM P-8179, FERM BP-1013; and *Bacillus sp.* SCRC-114D, FERM BP-1011.

12. A process for production of L-amino acid having the general formula (I):

wherein $R_1$ represents hydrogen, or methyl; and $R_2$ represents a linear or branched optionally substituted alkyl having 1 to 4 carbon atoms, or an optionally substituted aromatic group,
characterized by reacting a α-ketocarboxylic acid having the general formula (II):

wherein $R_1$ and $R_2$ are the same as defined above, or a salt thereof, ammonium ion, and NADH in the presence of L-phenylalanine dehydrogenase derived from microorganism belonging to the species *Sporosarcina ureae* or the genus Bacillus to form L-amino acid, and recovering the L-amino acid.

13. A process according to claim 12, wherein the phenylalanine dehydrogenase is present in a form selected from the group consisting of purified enzyme, partially purified enzyme preparation, disrupted cells, dried cells containing the enzyme, living cells, cultured broth, and an immobilized enzyme preparation.

14. A process according to claim 12, wherein a further NADH regenerating system is involved.

15. A process according to claim 14, wherein the NADH regenerating system is selected from the group consisting of a combination of formate dehydrogenase and formic acid or a salt thereof, a combination of L-glutamate dehydrogenase and L-glutamic acid or a salt thereof, a combination of alcohol dehydrogenase and ethanol, a combination of aldehyde dehydrogenase and acetaldehyde, and a combination of glucose-6-phosphate dehydrogenase and glucose-6-phosphate.

16. A process for production of L-amino acid having the general formula (I):

wherein $R_1$ represents hydrogen, or methyl; and $R_2$ represents a linear or branched optionally substituted alkyl having 1 to 4 carbon atoms, or an optionally substituted aromatic group, characterized by reacting a α-ketocarboxylic acid having the general formula (II):

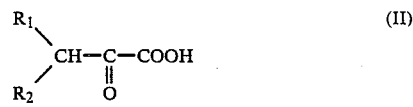

wherein $R_1$ and $R_2$ are the same as defined above, or a salt thereof, and an ammonium ion in the presence of cultured broth, living cells or cells treated in an extent wherein enzyme systems necessary for the conversion of α-ketocarboxylic acid to a corresponding L-amino acid remain, derived from a microorganism belonging to the species *Sporosarcina ureae* and capable of producing L-phenylalanine dehydrogenase, and in the presence of an energy source to form L-amino acid, wherein the L-phenylalanine dehydrogenase characterized by:

(1) catalyzing a reaction wherein L-phenylalanine, $NAD^+$ and $H_2O$ react to form phenylpyruvate, NADH and ammonium ion, and reverse reaction thereof; and (2) having a molecular weight of about 290,000 as determined by high performance liquid chromatography and a molecular weight of about 305,000 as determined by a sedimentation equilibrium method, and exhibiting a sub-unit with a molecular weight of about 38,000 to 39,000 as determined by SDS-polyacrylamide gel electrophoresis.

17. A process according to claim 16, wherein the energy source is selected from the group consisting of sugars, alcohols, organic acids or salts thereof, and a combination thereof.

18. A process according to claim 17, wherein the energy source is selected from the group consisting of arabinose, ribose, ribulose, xylose, fucose, rhamnose, fructose, galactose, gluconate, trehalose, glucose, mannitol, mannose, sorbitol, sorbose, inositol, lactose, maltose, sucrose, raffinose, glycerine, starches, inulin, glycogen, carboxymethyl cellulose, ethanol, methanol, propionic acid, acetic acid, formic acid, citric acid, pyruvic acid, succinic acid, malic acid, and α-ketoglutaric acid.

19. A process according to claim 18, wherein the *Sporosarcina ureae* is selected from the group consisting of *Sporosarcina urea* SCRC-R04, FERM P-8178, FERM BP-1012; *Sporosarcina ureae* IFO 12698; and *Sporosarcina ureae* IFO 12699, ATCC 6473.

* * * * *